United States Patent [19]

Boden et al.

[11] Patent Number: 4,515,987
[45] Date of Patent: May 7, 1985

[54] PROCESS FOR PREPARING A METHOXYBENZALDEHYDE FROM THE CORRESPONDING PHENOLIC BENZALDEHYDE

[75] Inventors: Richard M. Boden, Ocean; Theodore J. Tyszkiewicz, Sayreville; Michael Licciardello, Farmingdale; Manfred H. Vock, Locust; Joaquin F. Vinals, Rumson; Patrick Whalen, Matawan; Marie R. Hanna, Hazlet, all of N.J.

[73] Assignee: International Flavors & Fragrances Inc., New York, N.Y.

[21] Appl. No.: 624,757

[22] Filed: Jun. 26, 1984

Related U.S. Application Data

[62] Division of Ser. No. 496,568, May 20, 1983, abandoned, which is a division of Ser. No. 384,924, Jun. 4, 1982, abandoned.

[51] Int. Cl.³ .............................................. C07C 45/61
[52] U.S. Cl. ..................................... 568/433; 260/463; 549/438; 568/442; 426/534; 426/617; 426/599; 426/3; 514/974; 514/835; 252/522 R; 252/174.11; 106/316; 523/102; 131/276
[58] Field of Search ................................ 568/433, 435

[56]  References Cited
PUBLICATIONS

Wagner et al., Synthetic Organic Chemistry (1953), 226–229.

Primary Examiner—Bernard Helfin
Attorney, Agent, or Firm—Arthur L. Liberman

[57]  ABSTRACT

Described is a genus of compounds defined according to the structure:

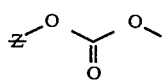

(Z) represents one of the moieties

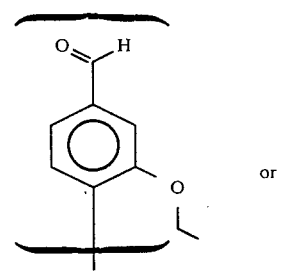

or

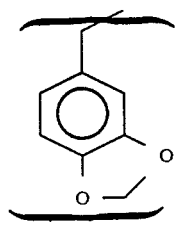

as well as the substantially pure compound defined according to the structure:

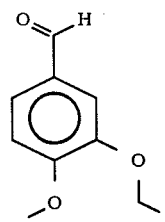

and the use thereof for augmenting or enhancing the aroma or taste of consumable materials including foodstuffs, chewing gums, medicinal products, toothpastes, chewing tobaccos, smoking tobaccos, smoking tobacco articles, perfumes, colognes and perfumed articles including solid or liquid anionic, cationic, nonionic or zwitterionic detergents, fabric softeners, fabric softener articles, perfumed articles, hair preparations and the like.

1 Claim, 8 Drawing Figures

IR SPECTRUM FOR EXAMPLE I.

GLC PROFILE FOR EXAMPLE II.
CRUDE

IR SPECTRUM FOR PEAK 32 OF FIG. 3 OF EXAMPLE II.

GLC PROFILE FOR EXAMPLE II.
FINAL PRODUCT

NMR SPECTRUM FOR FRACTION 7 OF EXAMPLE II

IR SPECTRUM FOR EXAMPLE II.

PROCESS FOR PREPARING A METHOXYBENZALDEHYDE FROM THE CORRESPONDING PHENOLIC BENZALDEHYDE

This is a divisional of application Ser. No. 496,568, filed 5/20/83, which, in turn, is a divisional of application for U.S. Letters Patent, Ser. No. 384,924 filed 6/4/82, now abandoned.

BACKGROUND OF THE INVENTION

The present invention relates to the compound defined according to the structure:

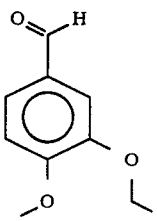

as well as compounds defined according to the genus:

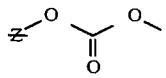

wherein Z represents one of the moieties:

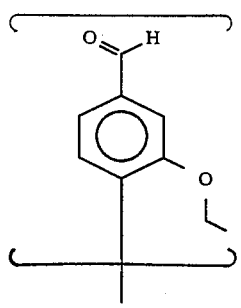

or

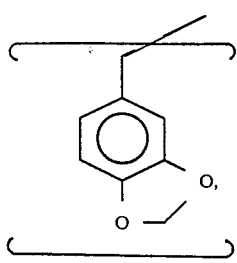

use of the compound having the structure:

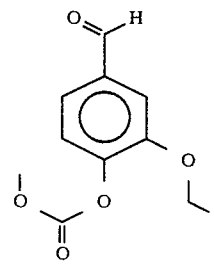

as an intermediate for producing the compound having the structure:

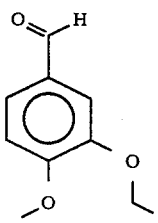

and uses of the foregoing compounds in augmenting or enhancing the aroma or taste of consumable materials such as foodstuffs, chewing gums, toothpastes, medicinal products, chewing tobaccos, perfumed compositions, perfumed articles, smoking tobacco compositions or smoking tobacco articles. Also the present invention relates to a process for producing the compound having the structure:

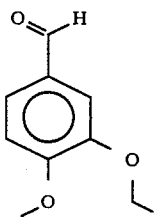

by rearranging the compound having the structure:

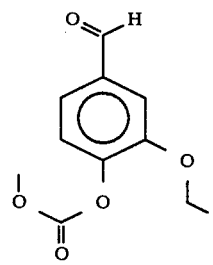

There has been considerable work performed relating to substances which can be used to impart (augment or enhance) flavors and fragrances to (or in) various consumable materials. These substances are used to diminish the use of natural materials some of which may be in short supply and to provide more uniform properties in the finished product.

Vanilla-like, sweet, fruity, raspberry, anisic, ionone-like, and jammy aroma and taste characteristics are highly desirable for many uses in foodstuff, chewing gum, toothpaste, medicinal product and chewing tobacco flavors.

Vanilla-like, raspberry-like and ionone-like aroma nuances are highly desirable in several types of perfume compositions, colognes and perfumed articles, e.g., perfumed polymers and anionic, cationic, nonionic and zwitterionic solid or liquid detergents.

Sweet, vanilla-like, heliotropin-like, fruity, juicy, rum, and sugary nuances are highly desirable in smoking tobacco prior to smoking and sweet, smoothing rich, vanilla-like, creamy, rum-like, fruity and caramellic aroma and taste nuances are high desirable in smoking tobacco on smoking in the main stream and in the side stream.

Specifically, a need has arisen for the use of powerful and long lasting vanilla type aroma and taste compounds and raspberry-like compounds in consumable materials in view of the need to use much smaller quantities than when using the heretofore known vanilla-like and raspberry-like aroma and/or taste imparting and/or augmenting compounds.

Fenaroli's Handbook of Flavor Ingredients, Second Edition, Vol. 2, Published by the CRC Press of Cleveland, Ohio discloses at page 196 the use in flavor of ethyl vanillin having the structure:

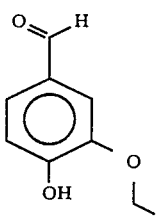

indicating that it has "an intense vanilla odor and sweet taste". It further is indicated that the flavoring power of this compound is 2-4 times stronger than vanillin. Fenaroli's Handbook of Flavor Ingredients also indicates at page 561 that veratraldehyde having the structure:

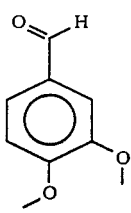

has a use in food flavors and has a very sweet, woody, vanilla-like odor and a warm, sweet and vanilla-like taste. Fenaroli's Handbook of Flavor Ingredients also indicates at page 560 that vanillin itself having the structure:

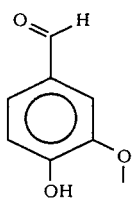

has a strong vanilla-like odor and a very sweet taste and is useful in augmenting or enhancing the aroma or taste of foodstuffs, chewing gums and the like.

Arctander "Perfume and Flavor Chemicals (Aroma Chemicals)" published in 1969, at monograph 1363, also indicates the use in food flavors and fragrances of ethyl vanillin having the structure:

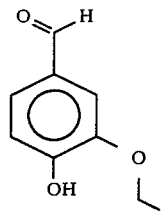

and Arctander further indicates "ethyl vanillin is often used to substitute a larger amount of vanillin in the fragrance when a discoloration problem arises due to the active hydroxyl or aldehyde groups of the vanillin-/ethyl vanillin molecules". Arctander also discloses a monograph 1364, isoethyl vanillin having the structure:

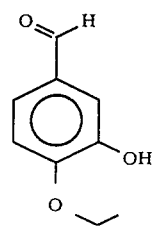

and indicates that it has a "sweet, somewhat floral odor remotely reminiscent of vanilla but much weaker than ethyl vanillin and also weaker than vanillin". Arctander further indicates at monograph 1365, that 3-methoxy-4-ethoxy benzaldehyde otherwise known as "Homo veratraldehyde" having the structure:

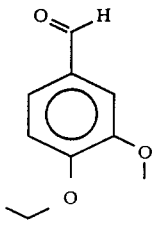

has a sweet, somewhat floral odor remotely reminiscent of vanilla, more so than commercial ethyl vanillin, but not with the same strength and has a sweet, vanilla-like taste of approximately two times the power effect of vanillin. At monograph 3067, Arctander indicates the use of vanillin itself in foodstuffs and fragrances. At monograph 3068, Arctander indicates the use in flavors and fragrances of isovanillin having the structure:

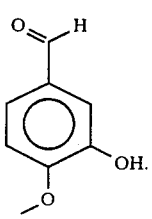

Arctander indicates that "isovanillin" is practically odorless when cold; mild, floral, herbaceous or Hay-like at room temperature, and very sweet, balsamic-Vanilla-like when heated above 60° C. Arctander also indicates that the material as such is rarely used in perfumes or flavors since its aromatic value is too inconspicuous, but it has some importance since it occurs along with Vanillin in one of the many processes used for the manufacture of vanillin.

European Published Patent Application No. 31253, published on July 1, 1981, entitled "Process for preparing 3,4-substituted benzaldehydes" (assigned to the Sumitomo Chemical Company, Limited of Japan) discloses a genus of compounds defined according to the structure:

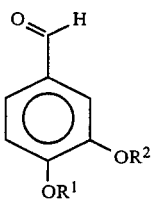

wherein $R_1$ and/or $R_2$ represent hydrogen or alkyl having from one up to four carbon atoms or $R_1$ or $R_2$ may jointly form an alkylene group having from one to four carbon atoms. The compound having the structure:

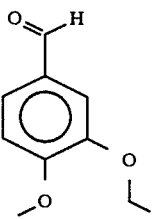

is specifically set forth in a list located in claim 18 on page 34 of said published application, and furthermore the compound having the structure:

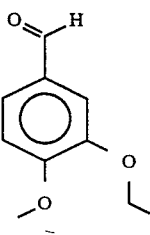

is also specifically set forth at lines 30 and 31 on page 21 of said application. No organoleptic characterization is given for the compound nor is a specific method of preparation for said compound set forth or exemplified in said published European Patent Application No. 31253. Indeed, the compound is not characterized in any way whatsoever except for naming it in a large list of compounds contained within the generic structure:

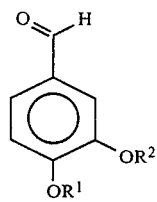

Beilstein, Volume E II 8, page 283, System No. 773, discloses 4-Methoxy-3-athoxy-benzaldehyde having the structure:

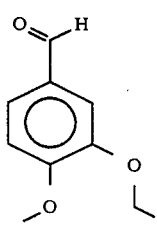

and indicates that it is a crystal having a melting point of 50°–51° C. and can be prepared by reaction of isovanillin and ethyl iodide.

Beilstein, Volume E III 8, at page 2024, also indicates that the compound having the structure:

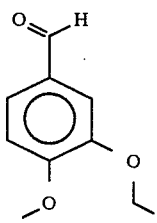

can be prepared by reacting 3-hydroxy-4-methoxy-benzaldehyde with diethyl sulfate in the presence of sodium hydroxide or methanolic KOH.

Chem. Abstracts, Vol. 25, at pages 3325 and 3326 (1931) indicates that the compound having the structure:

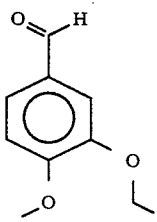

has a pronounced vanillin odor. This abstract is of Ber. 64B, 274–80 (1931).

Nothing in the prior art however discloses any compound defined according to the structure:

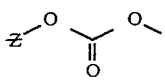

wherein Z is represented by one of the moieties:

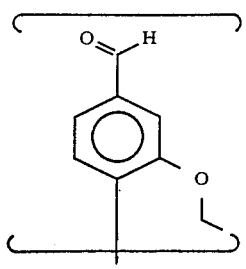

or

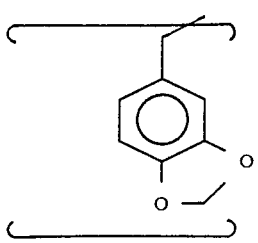

or organoleptic uses thereof.

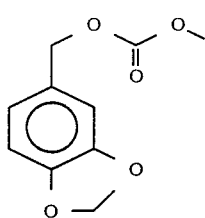

(solvent: CFCl$_3$; field strength 100 MHz).

Figure 2:
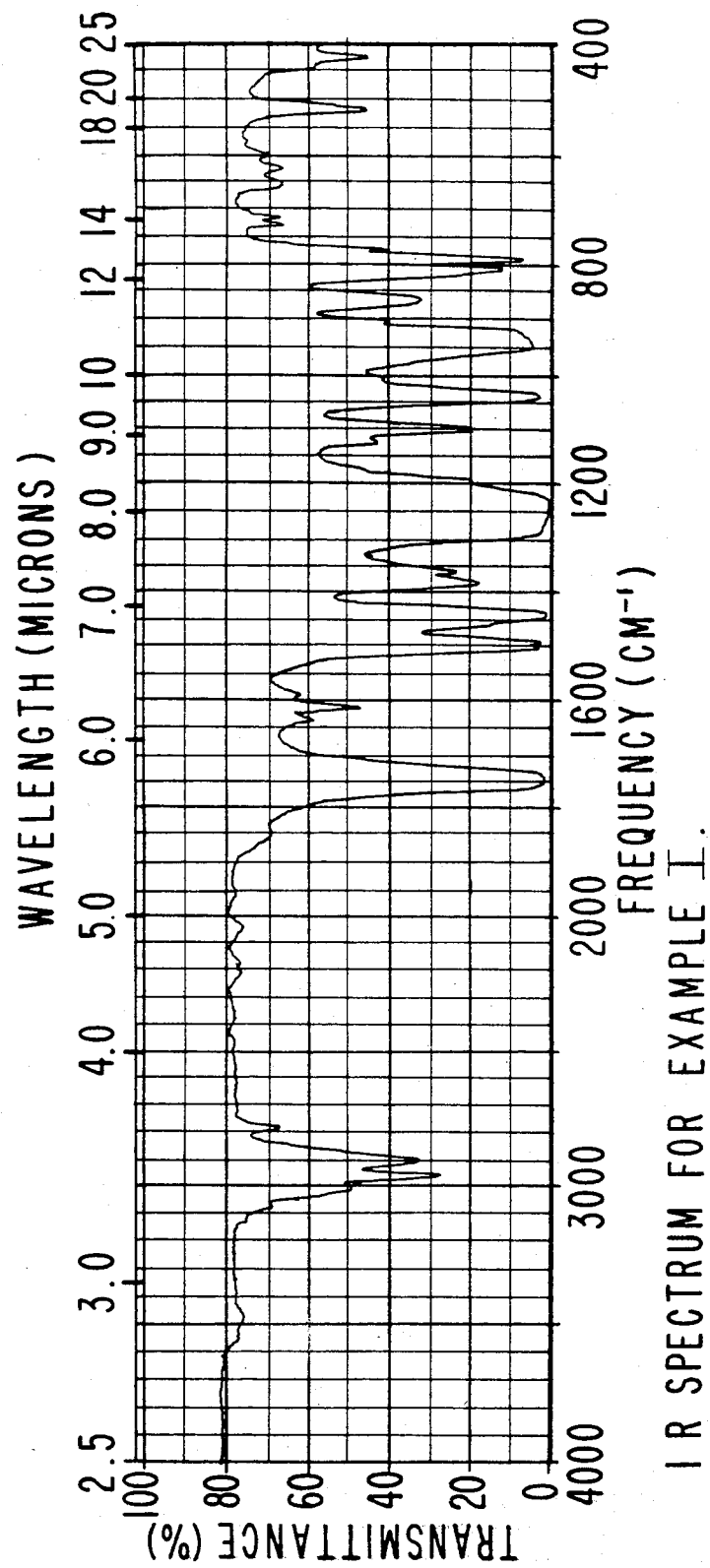

FIG. 2 is the infra-red spectrum for the compound produced according to Example I having the structure:

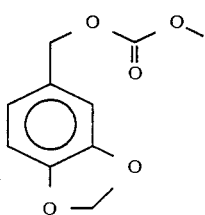

Figure 3:
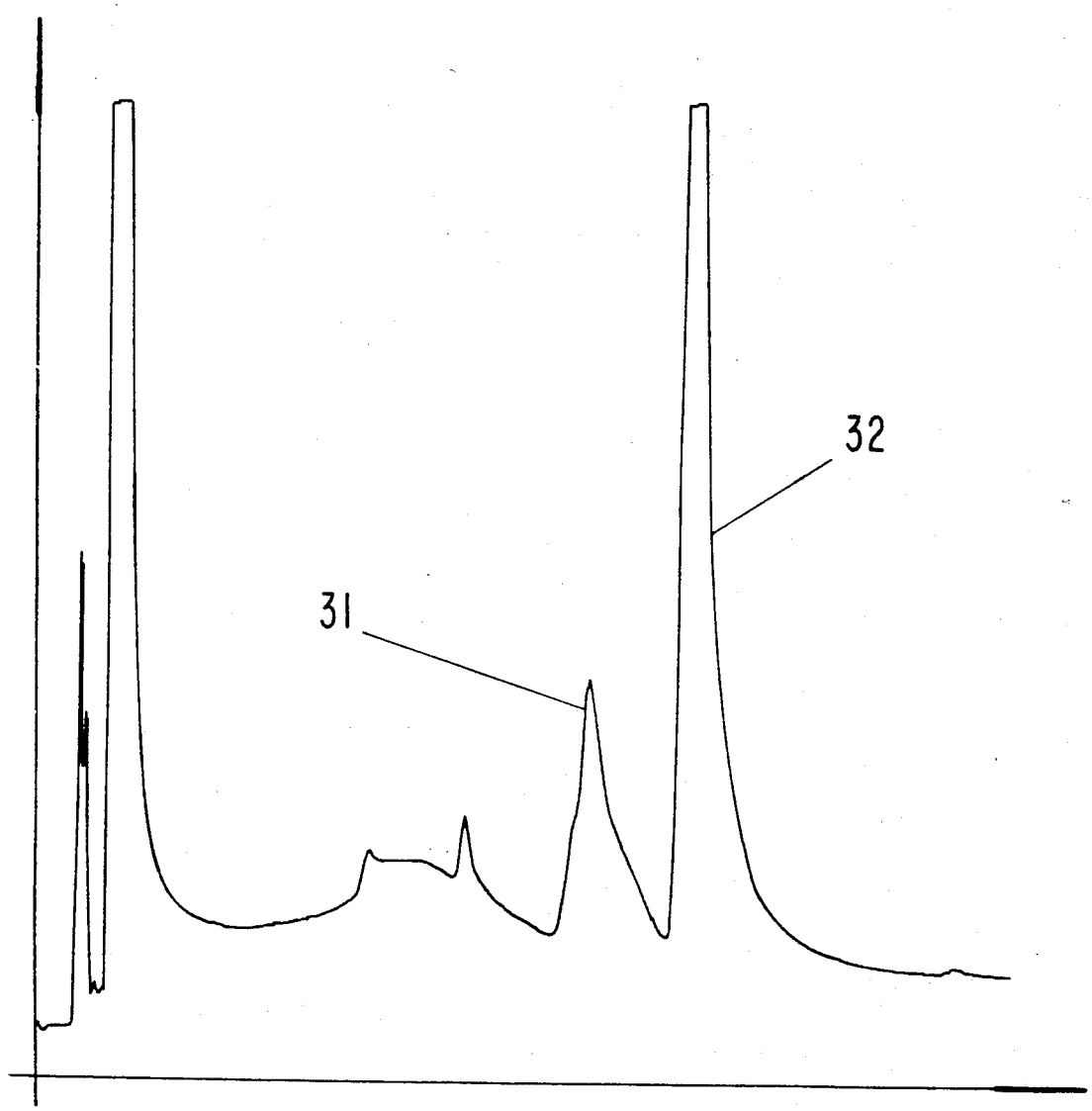

FIG. 3 is the GLC profile for the crude reaction product of Example II containing the compound having the structure:

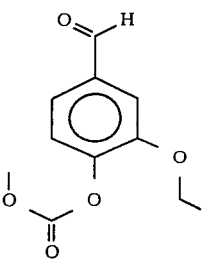

as well as the starting material having the structure:

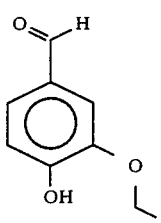

Figure 4:
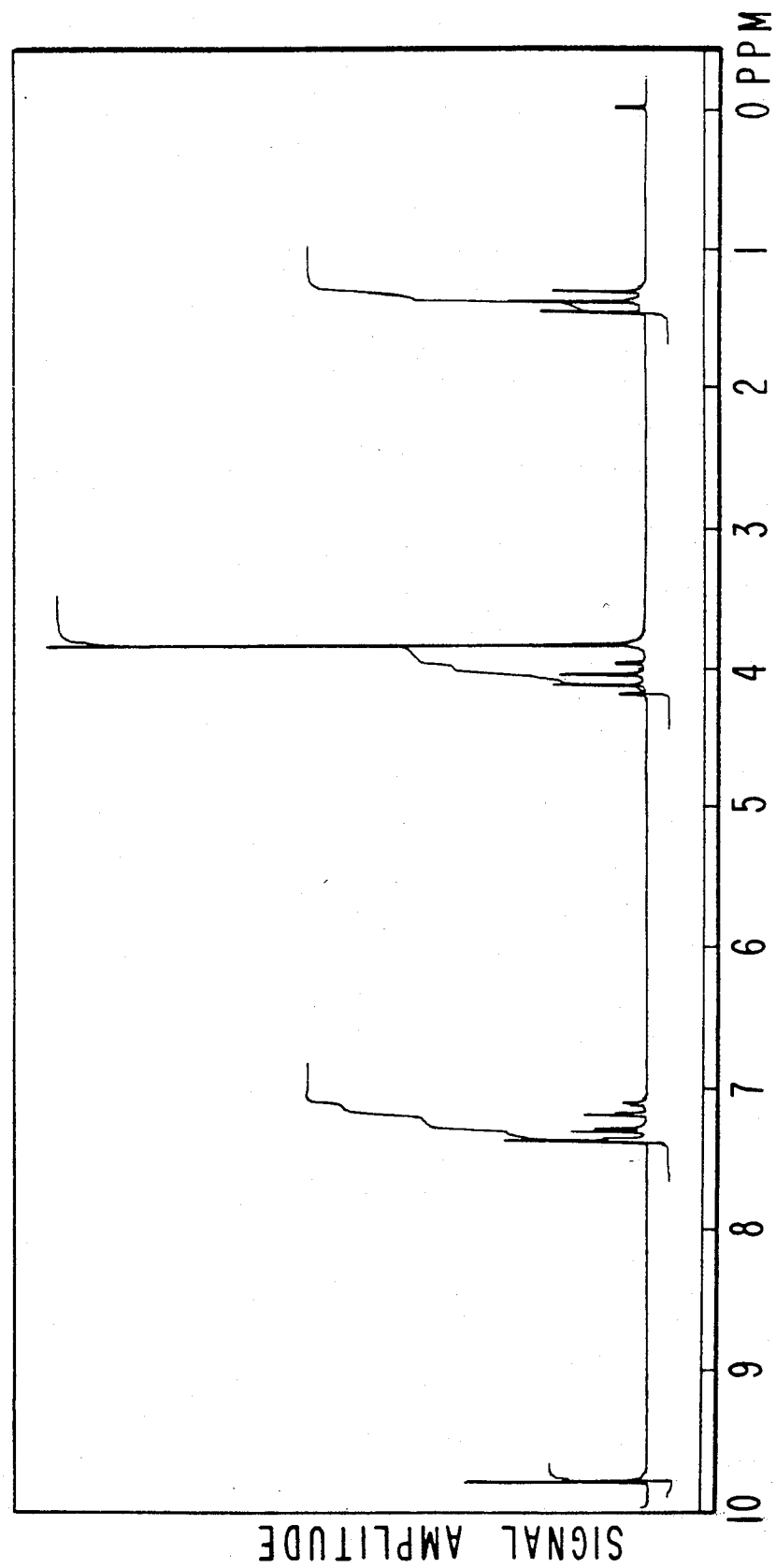

FIG. 4 is the NMR spectrum for the peak indicated by reference 32 of the GLC profile of FIG. 3 for the compound having the structure:

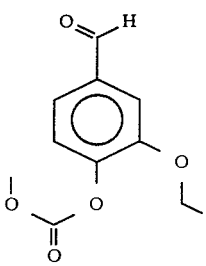

(solvent: CFCl$_3$; field strength 100 MH$_z$).

Figure 5:
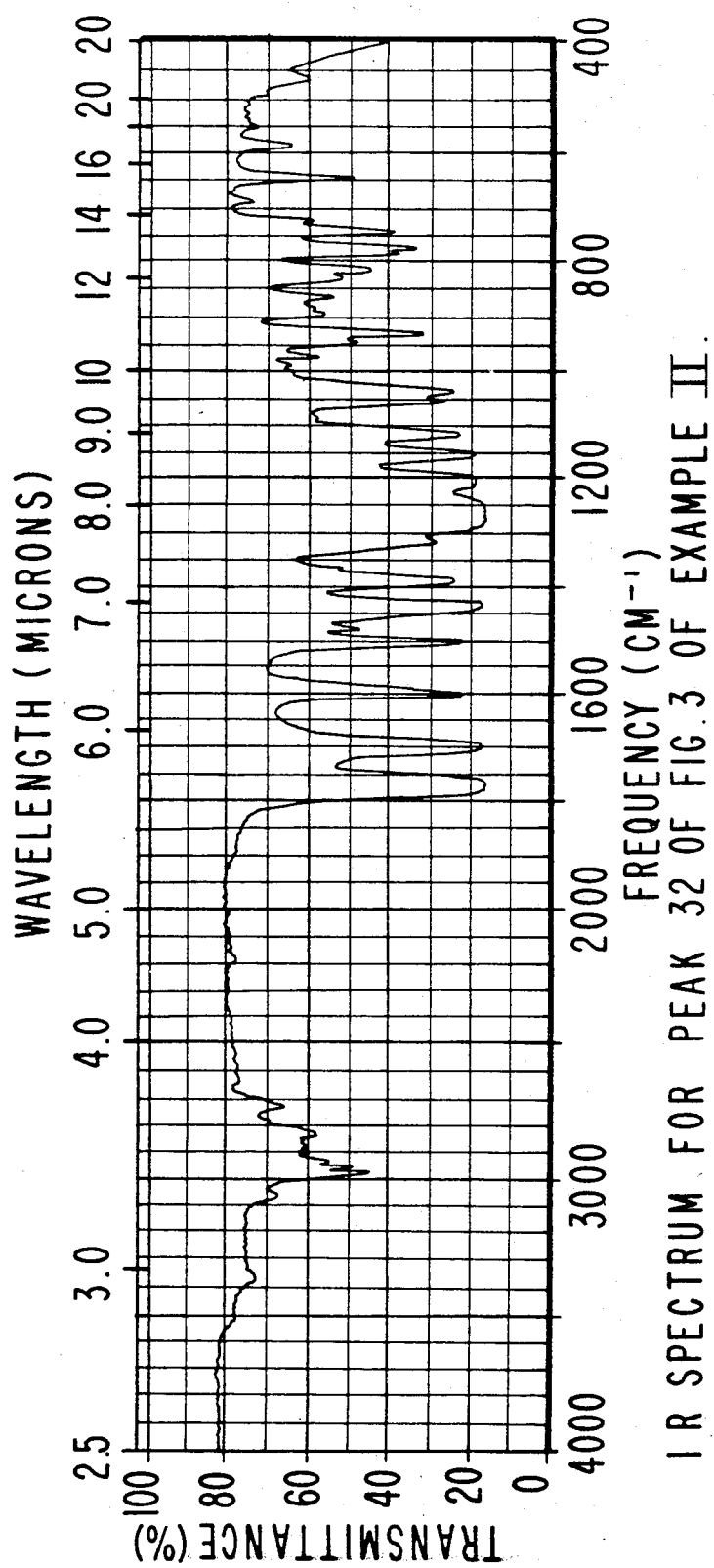

FIG. 5 is the infra-red spectrum for the peak indicated by reference 32 on the GLC profile of FIG. 3 and is for the compound having the structure:

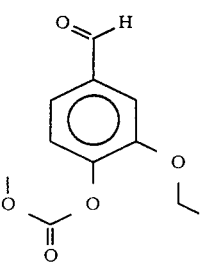

Figure 6:
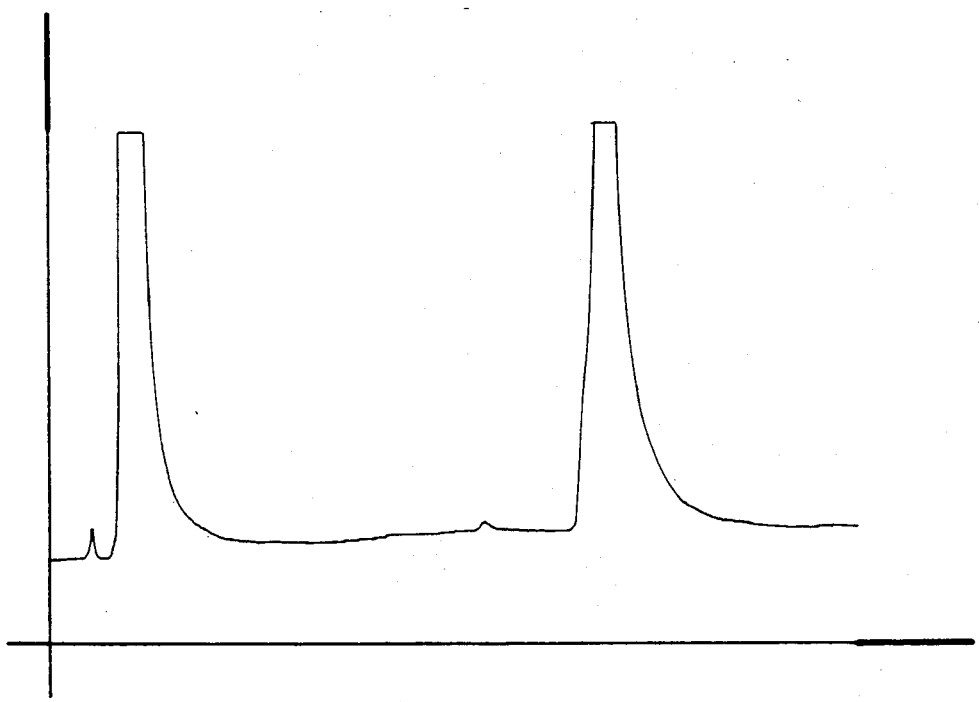

FIG. 6 is the GLC profile for the final product produced according to Example II which is the compound having the structure:

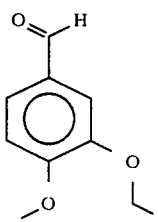

Figure 7:
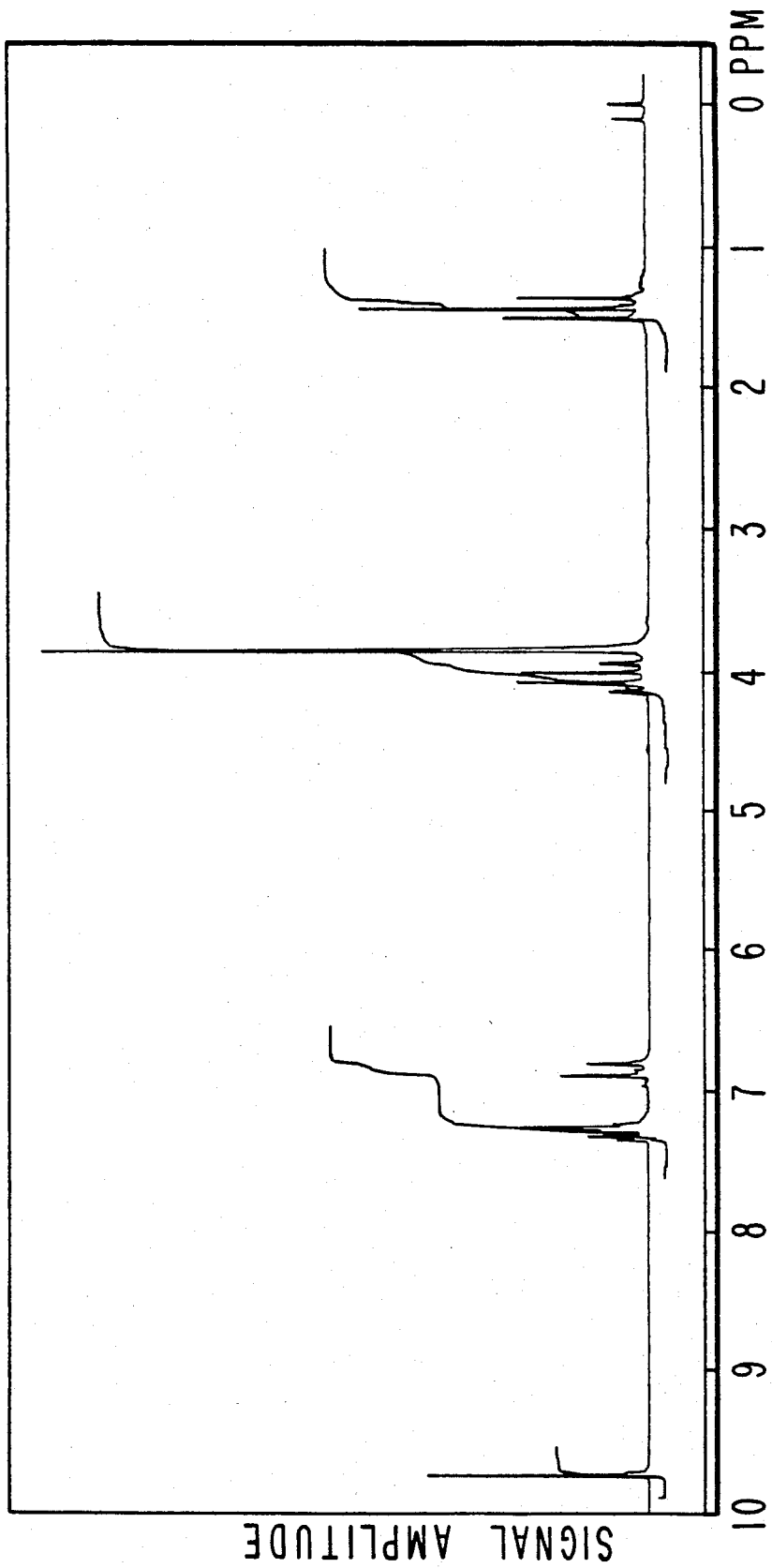

FIG. 7 is the NMR spectrum for fraction 7 of the distillation product of the reaction product of Example II consisting of the compound having the structure:

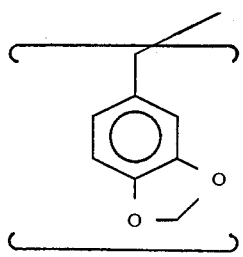

(solvent: CFCl₃; field strength 100 MH$_z$).

Figure 8:
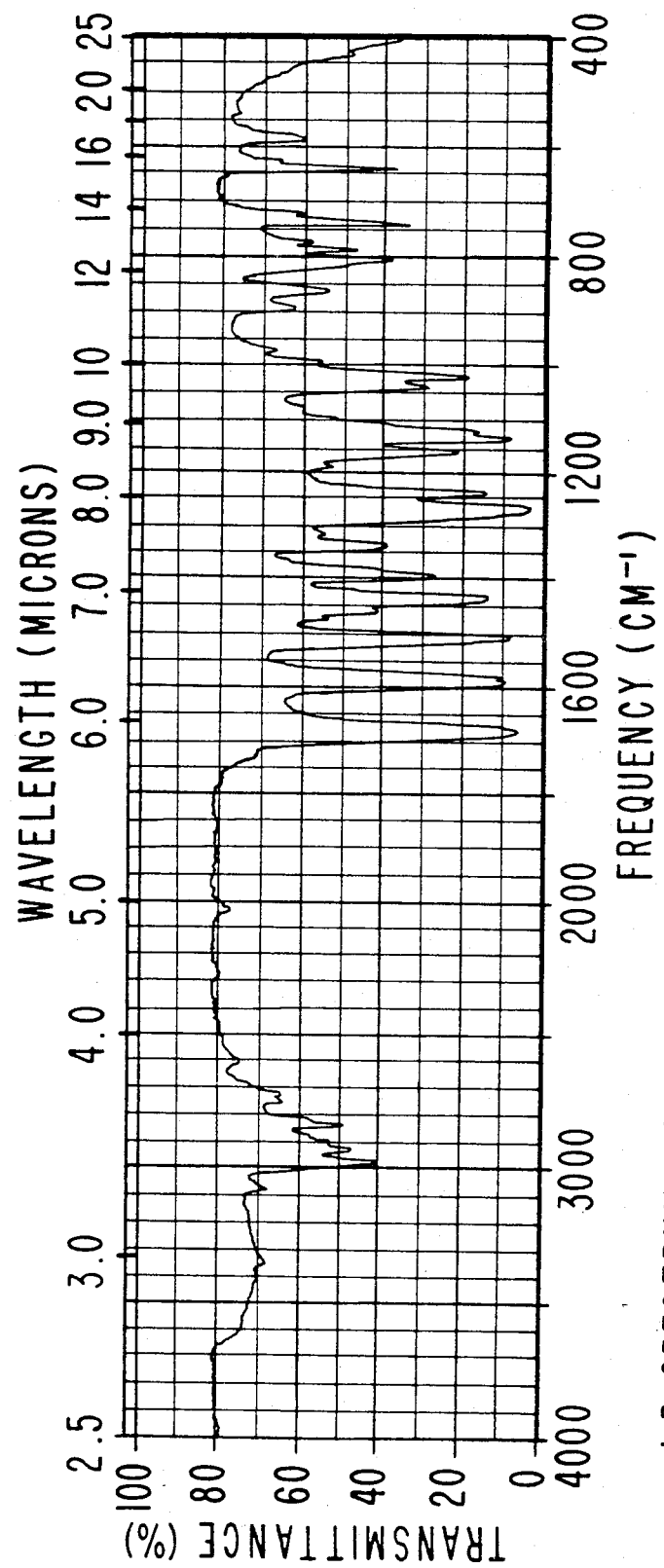

FIG. 8 is the infra-red spectrum for fraction 7 of the distillation product of the reaction product of Example II containing the compound having the structure:

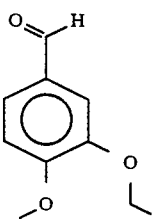

DETAILED DESCRIPTION OF THE DRAWINGS

FIG. 3 is the GLC profile for the crude reaction product (first stage) of Example II. The peak indicated by reference 31 is for the starting material having the structure:

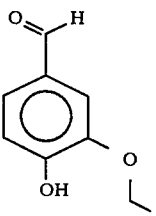

The peak indicated by the reference 32 is for the reaction product, first stage, having the structure:

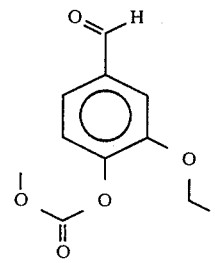

The conditions for running this GLC curve are: 12% SF-96, col., 6'×¼", programmed from 100° to 220° C. at 8° C. per minute.

THE INVENTION

It has now been discovered that novel solid and liquid foodstuff, chewing gum, toothpaste, medicinal product and chewing tobacco compositions therefor having vanilla-like, sweet, fruity, raspberry-like, anisic and jammy aroma and taste nuances; and novel perfume compositions, perfumed articles (such as solid or liquid anionic, cationic, nonionic or zwitterionic detergents, fabric softener compositions, disposable fabric softener articles, cosmetic powders and perfumed polymers) and colognes having natural and diffusive sweet, fruity, raspberry, anisic, ionone-like aroma profiles; as well as novel smoking tobaccos and smoking tobacco flavoring compositions having, prior to smoking, sweet, vanilla-like, coumarin-like, creamy, heliotropine-like, fruity, juicy and rum nuances and on smoking in both the main stream and the side stream, sweet, smoothing rich, coumarin-like, rum-like and caramellic aroma and taste nuances may be provided by the utilization of compounds defined according to the structure:

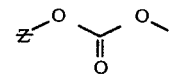

wherein Z is one of the moieties:

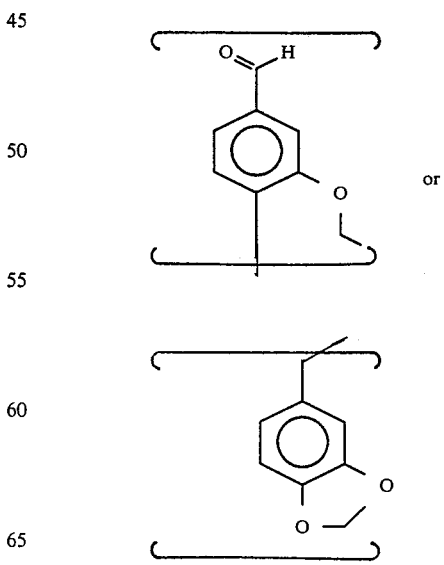

or by the compound having the structure:

The compound having the structure:

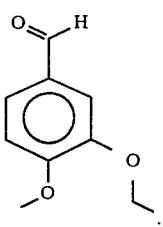

The compound having the structure:

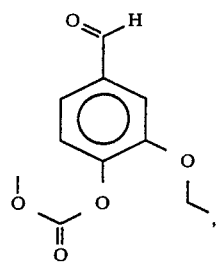

furthermore, is a novel intermediate for producing the compound having the structure:

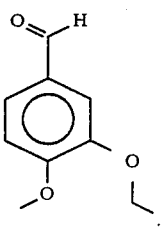

The compound defined according to the structure:

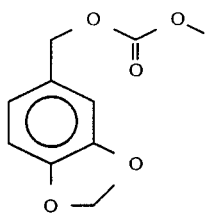

may be prepared by reacting dimethyl carbonate having the structure:

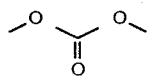

with heliotropyl acetate having the structure:

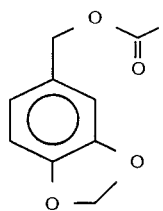

according to the reaction:

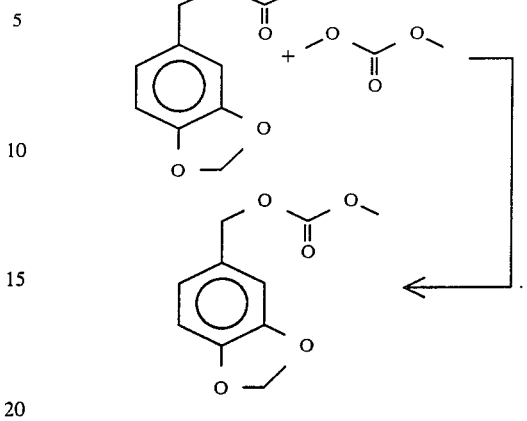

This reaction takes place in the presence of an alkali metal alkoxide such as sodium methoxide, sodium ethoxide, potassium ethoxide, potassium methoxide, potassium ethoxide or potassium t-butoxide.

The temperature of reaction may vary from about 70° C. up to about 120° C. with a preferred temperature of reaction of 80°–95° C.

The mole ratio of dimethyl carbonate:heliotropyl acetate may vary from about 2.5:1 down to about 1:1 with a preferred mole ratio of dimethyl carbonate:heliotropyl acetate of about 2:1.

The mole ratio of alkali metal alkoxide:dimethyl carbonate may vary from about 1:20 down to about 1:5.

During the reaction, methyl acetate is generated which is preferably distilled out of the reaction mass using appropriate equipment.

At the end of the reaction, the reaction mass is "worked up" using standard extraction and fractional distillation techniques.

The compound having the structure:

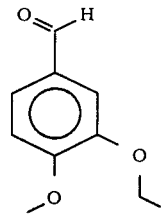

is prepared from the compound having the structure:

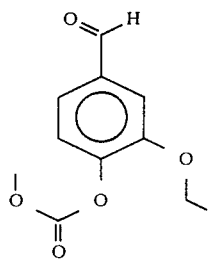

which, in turn, is prepared by reacting the compound having the structure:

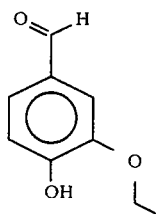

with methyl chloroformate.

The reaction of methyl chloroformate with the compound having the structure:

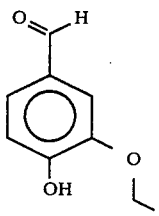

is in accordance with the following reaction:

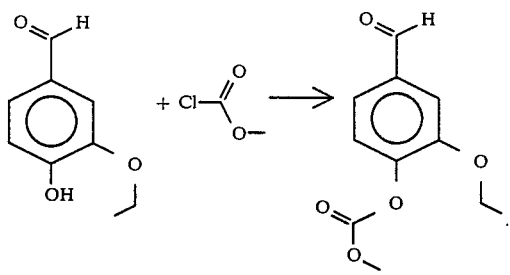

The reaction of the compound having the structure:

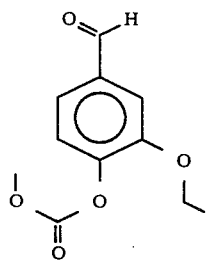

to form the compound having the structure:

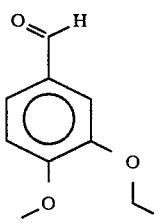

is as follows:

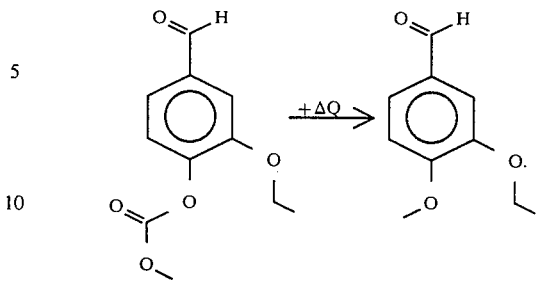

In carrying out the reaction:

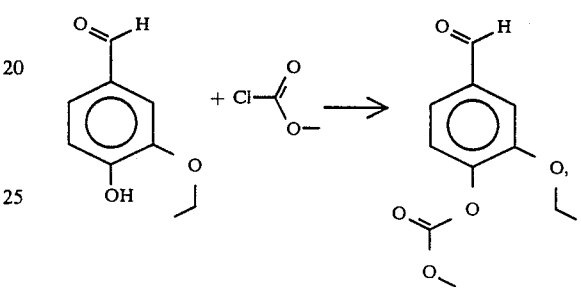

the reaction takes place in the presence of a solvent which is inert to the reactants and the reaction product, for example, methyl ethyl ketone or acetone. The reaction takes place using a phase transfer catalyst such as Aliquat®336 (trimethyl capryl ammonium chloride manufactured by Henkel Chemical Company of Minneapolis, Minn.).

The reaction temperature is at reflux and the refluxing conditions depend upon the nature and quantity of solvent utilized. When using methyl ethyl ketone, the reaction temperature is in the range of about 65°–75° C. at atmospheric pressure and higher temperatures if higher pressures are used.

The reaction takes place in the presence of base such as sodium carbonate, potassium carbonate, or lithium carbonate.

The mole ratio of methyl chloroformate: the compound having the structure:

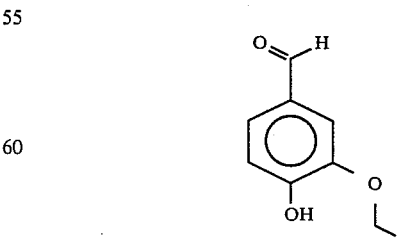

may vary from about 3:1 down to about 1:1 with a mole ratio of about 1.4:1 being preferred. The concentration of the compound having the structure:

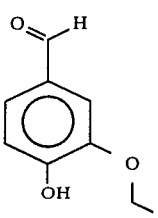

in the reaction mass may vary from about 1 mole per liter up to about 3 moles per liter with a concentration of about 1.8 moles per liter of compound having the structure:

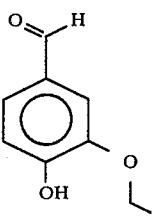

being preferred. The mole ratio of base such as sodium carbonate: the compound having the structure:

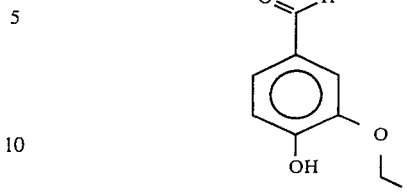

may vary from about 2:1 down to about 1:1 with a mole ratio of 1:1 being preferred.

The concentration of phase transfer agent such as Aliquat ®336 based on total weight of the reaction mass (on a solvent-free basis) may vary from about 0.2% up to about 2.0% with a concentration of about 0.9% up to about 1.1% phase transfer catalyst being preferred (on a solvent-free basis).

The following table sets forth the organoleptic properties of the compounds of our invention:

TABLE I

| Structure of Compound | Food Flavor Properties | Fragrance Properties | Smoking Tobacco Flavor Properties |
|---|---|---|---|
|  | Sweet, fruity, raspberry kernel, anisic raspberry jam-like aroma and taste with cooked strawberry jam nuances at 8 ppm. | A sweet, fruity, raspberry-like, anisic-like, ionone-like aroma profile. | A fruity, rum-like, sweet aroma and taste profile both prior to and on smoking in the main stream and the side stream giving rise to natural fresh, aromatic tobacco nuances. |
|  | An intense, natural vanilla and coumarin aroma taste and profile. The vanilla notes are approximately 4 times the strength of that of vanillin. | A characteristic intense vanilla-like aroma having a strength of about 4 times that of vanillin. | A sweet, creamy aroma and taste both prior to and on smoking in the main stream and in the side stream. |
|  | A brown sugar, anisic vanilla aroma profile with a smokey, anisic, vanilla, sweet, phenolic taste profile causing it to be useful in vanilla, malt, chocolate and chicle gum flavors. The vanilla notes are approximately 4 times the strength of the precursor compound having the structure: | A characteristic intense vanilla-like aroma having a strength of about 16 times that of vanillin and having the property that it does not give rise to any discoloration particularly in perfumed articles such as soap. | A sweet, coumarin-like creamy aroma and taste both prior to and on smoking in the main stream and in the side steam. |

TABLE I-continued

| Structure of Compound | Food Flavor Properties | Fragrance Properties | Smoking Tobacco Flavor Properties |
|---|---|---|---|
| 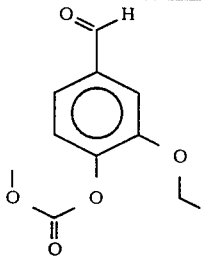 | and approximately 15-20 times the strength of vanillin having the structure:<br>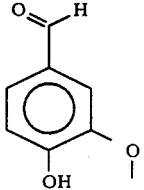<br>In addition, this compound does not cause discoloration as does vanillin in foodstuffs, chewing gums and other functional products. | | |

In the section of the instant application infra, the compounds having the structures:

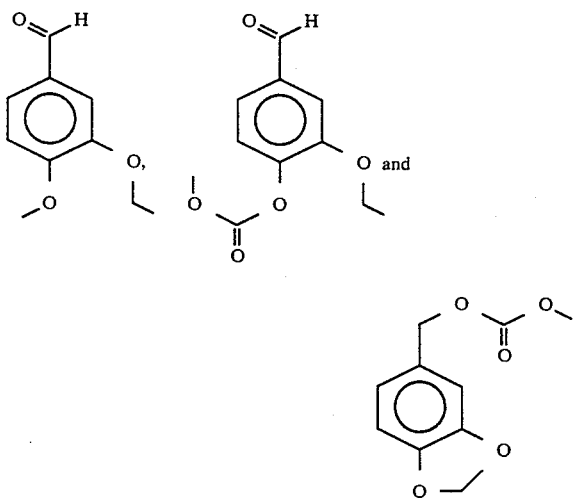

will collectively be referred to as "oxybenzene derivatives".

The oxybenzene derivatives of our invention are capable individually and taken together of supplying and/or potentiating certain flavor and aroma notes usually lacking in many fruit flavors as well as vanilla flavors heretofore. Further, the oxybenzene derivatives of our invention taken individually or together are capable of supplying certain fragrance notes usually lacking in many perfumery materials, for example, Fougèere formulations, lavendin formulations, citrusy formulations and oakmoss-type formulations. In addition, this material is capable of acting as a fixative in perfumery while augmenting or enhancing certain aroma nuances itself.

As used herein, the term "foodstuff" includes both solid and liquid ingestible materials which usually do, but need not, have nutritional value. Thus, foodstuffs includes soups, convenience foods, beverages, dairy products, candies, vegetable cereals, soft drinks, snacks and the like.

As used herein, the term "medicinal products" includes both solids and liquids which are ingestible nontoxic materials which have medicinal value such as cough syrups, cough drops and chewable medicinal tablets.

The term "chewing gum" is intended herein to be a foodstuff composition comprising a substantially water-insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g. glycerine and a flavoring composition which incorporates one or more of the oxybenzene derivatives of our invention and, in addition, sweetening agents which may be sugars, including sucrose or dextrose and/or artificial sweeteners such as cyclamates or saccharin. Other optional ingredients may be present.

The term "augment" in its various forms is used herein to mean the supplying, modifying or imparting of a flavor or aroma characteristic note or nuance to an otherwise bland, relatively tasteless or non-odorous substance or modifying an existing flavor or aroma characteristic where the natural flavor is deficient in some regard, or supplementing the existing flavor or aroma impression to modify its quality, character, taste or aroma.

The term "enhance" is used herein to mean the intensification of a flavor or aroma characteristic or note without the modification of the quality thereof. Thus, "enhancement" of a flavor or aroma means that the enhancement agent does not add any additional flavor note or nuance.

Substances suitable for use herein as co-ingredients or flavoring adjuvants are well known in the art for such use, being extensively described in the relevant literature. It is required that any such material be "ingestibly acceptable" and thus non-toxic or otherwise non-deleterious, particularly from an organoleptic standpoint whereby the ultimate flavor and/or aroma of the consumable material used does not cause the consumable material to have unacceptable aroma and taste nuances.

It is a further requirement that such material be organoleptically compatible with the foodstuff with which it is used so that the flavor and aroma nuances of such material, taken together with the flavor and aroma nuances of the foodstuff (as a whole) give rise to a harmoniously aesthetically pleasing aroma and taste profile. Such material, in general, may be characterized as flavoring adjuvants or vehicles comprising broadly, stabilizers, thickeners, surface active agents, conditions, other flavorants and flavor intensifiers.

Stabilizer compounds include preservatives, e.g. sodium chloride; antioxidants, e.g. calcium and sodium ascorbate, ascorbic acid, butylated hydroxyanisole (mixture of 2- and 3-tertiary-butyl-4-hydroxyanisole), butylated hydroxy toluene (2,6-di-tertiary-butyl-4-methyl phenol), propyl gallate and the like and sequestrants, e.g. citric acid.

Thickener compounds include carriers, binders, protective colloids, suspending agents, emulsifiers and the like, e.g. agar agar, carrageenan, cellulose and cellulose derivatives such as carboxymethyl cellulose and methyl cellulose; natural and synthetic gums such as gum arabic, gum tragacanth, gelatin, proteinaceous materials; lipids; carbohydrates; starches, pectins and emulsifiers, e.g. mono- and diglycerides of fatty acids, skim milk powder, hexoses, pentoses, dissacharides, e.g. sucrose, corn syrup and the like.

Surface active agents include emulsifying agents, e.g. fatty acids such as capric acid, caprylic acid, palmitic acid, myristic acid and the like, mono- and diglycerides of fatty acids, lecithin, defoaming and flavor dispersing agents such as sorbitan monostearate, potassium stearate, hydrogenated tallow alcohol and the like.

Conditioners include compounds such as bleaching and maturing agents, e.g. benzoyl peroxide, calcium peroxide, hydrogen peroxide and the like, starch modifiers such as peracetic acid, sodium chlorite, sodium hypochlorite, propylene oxide, succinic anhydride and the like, buffers and neutralizing agents, e.g. sodium acetate, ammonium bicarbonate, ammonium phosphate, citric acid, lactic acid, vinegar and the like, colorants, e.g. carminic acid, cochineal, tumeric and curcumin and the like, firming agents such as aluminum sodium sulfate, calcium chloride and calcium glyconate, texturizers, anti-caking agents, e.g. aluminum calcium sulfate and tribasic calcium phosphate, enzymes, yeast foods, e.g. calcium lactate and calcium sulfate, nutrient supplements, e.g. iron salts such as ferric phosphate, ferrous gluconate and the like, riboflavin, vitamins, zinc sources such as zinc chloride, zinc sulfate and the like.

Other flavorants and flavor intensifiers include organic acids, e.g. acetic acid, formic acid, 2-hexenoic acid, benzoic acid, n-butyric acid, caproic acid, caprylic acid, cinnamic acid, isobutyric acid, isovaleric acid, alpha-methyl-butyric acid, propionic acid, valeric acid, 2-methyl-2-pentenoic acid, and 2-methyl-cis-3-pentenoic acid; ketones and aldehydes, e.g. acetaldehyde, acetophenone, acetone, acetyl methyl carbinol, acrolein, n-butanal, crotonal, diacetyl, beta,beta-dimethylacrolein, n-hexanal, 2-hexanal, cis-3-hexenal, 2-heptenal, 4-(p-hydroxyphenyl)-2-butanone, alpha-ionone, beta-ionone, 2-methyl-3-butanone, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1,cis-3-hexen-1-ol, 3-methyl-3-buten-1-ol, 1-pentenol, 1-penten-3-ol, p-hydroxyphenyl-2-ethanol, isoamyl alcohol, isofenchyl alcohol, phenyl-2-ethanol, alpha-terpineol, cis-terpineol hydrate, esters, such as butyl acetate, ethyl acetate, ethyl acetoacetate; ethyl benzoate, ethyl butyrate, ethyl caproate, ethyl cinnamate, ethyl crotonate, ethyl formate, ethyl isobutyrate, ethyl isovalerate, ethyl alpha-methyl-butyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, methyl-2-methyl-butyrate, propyl acetate, amyl acetate, amyl butyrate, benzyl salicylate, dimethyl anthranilate, ethyl methylphenylglycidate ethyl succinate isobutyl cinnamate and terpenyl acetate; essential oils such as jasmin absolute, rose absolute, orris absolute, lemon essential oil, Bulgarian rose, yara yara, natural raspberry oil and vanilla; lactones, sulfides, e.g. methyl sulfide and other materials such as maltol, acetoin and acetals (e.g. 1,1-diethoxyethane,1,1-dimethoxyethane and dimethoxymethane.

The specific flavoring adjuvant selected for use may be either solid or liquid depending upon the desired physical form of the ultimate product, i.e. foodstuff, whether simulated or natural, and should, in any event, be capable of providing an environment in which the cyclic chemical compounds can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g. simulated foodstuffs, ingredients capable of providing normally solid compositions should be selected such as various cellulose derivatives.

As will be appreciated by those skilled in the art, the amount of one or more of the oxybenzene derivatives of our invention employed in a particular instance can vary over a relatively wide range whereby its desired organoleptic effects (having reference to the nature of the product) are achieved. Thus, correspondingly greater amounts would be necessary in those instances wherein the ultimate food composition to be flavored is relatively bland to the taste, whereas relatively minor quantities may suffice for purposes of enhancing the composition merely deficient in natural flavor or aroma. The primary requirement is that the amount selected (to be effective) be sufficient to augment or enhance the organoleptic characteristics of the parent composition (whether foodstuff per se or flavoring composition).

The use of insufficient quantities of one or more of the oxybenzene derivatives of our invention will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, it is found that quantities of one or more of the oxybenzene derivatives of our invention ranging from a small but effective amount, e.g. 0.1 parts per million up to about 20 parts per million by weight based on total composition are suitable. Concentrations in excess of the maximum quantity stated are not normally recommended, since they fail to prove commensurate enhancement of organoleptic properties. In those instances, wherein the oxybenzene derivatives of our invention is added to the foodstuff as an integral component of a flavoring composition, it is, of course, essential that the total quantity of flavoring composition employed by sufficient to yield an effective oxybenzene derivatives concentration in the foodstuff product.

Food flavoring compositions prepared in accordance with the present invention preferably contain the oxybenzene derivatives in concentrations ranging from about 0.1% up to about 15% by weight based on the total weight of said flavoring composition.

The compositions described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing one or more of the oxybenzene derivatives of our invention with, for example, gum arabic, gum tragacanth, carrageenan and the like, and thereafter spray-drying the resultant mixture whereby to obtain the particulate solid product. Pre-prepared flavor mixes in powder form, e.g. a fruit flavored powdered mix, are obtained by mixing the dried solid components, e.g. starch, sugar and the like and one or more of the oxybenzene derivatives of our invention in a dry blender until the requisite degree of uniformity is achieved.

It is presently preferred to combine with the oxybenzene derivatives of our invention the following adjuvants:

p-Hydroxybenzyl acetone;
Geraniol;
Acetaldehyde;
Maltol;
Ethyl methyl phenyl glycidate;
Benzyl acetate;
Dimethyl sulfide;
Vanillin;
Methyl cinnamate;
Ethyl pelargonate;
Methyl anthranilate;
Isoamyl acetate;
Isobutyl acetate;
Alpha ionone;
Ethyl butyrate;
Acetic acid;
Gamma-undecalactone;
1-(3-(methylthio)butyryl-2,6,6-trimethyl cyclohexene;
1(3(methylthio)butyryl)-2,6,6-trimethyl-1,3-cyclohexadiene;
Naphthyl ethyl ether;
Diacetyl;
Ethyl acetate;
Anethole;
Isoamyl butyrate;
Cis-3-hexenol-1;
2-Methyl-2-pentenoic acid;
2-Methyl-cis-3-pentenoic acid;
Ethyl-2-methyl-cis-3-pentenoate;
Methyl-2-methyl-cis-3-pentenoate;
Elemecine (4-allyl-1,2,6-trimethoxy benzene);
Isoelemecine (4-propenyl-1,2,6-trimethoxy benzene); and
2-(4-hydroxy-4-methylpentyl)norbornadiene prepared according to U.S. Pat. No. 3,886,289, issued on May 27, 1975.

An additional aspect of our invention provides an organoleptically improved smoking tobacco product and additives therefor as well as methods for making the same which overcome specific problems heretofore encountered in which specific desired sweet, creamy, coumarin-like, smoothing ring, heliotropin-like, fruity, rum, sugary and caramellic flavor and aroma characteristics are created or enhanced and may be readily controlled and maintained at the desired uniform level regardless of variations in the tobacco components of the blend.

This invention further provides improved tobacco additives and methods whereby various desirable sweet, creamy, coumarin-like, heliotropin-like, fruity, juicy, rum-like, and caramellic aroma characteristics may be imparted to smoking tobacco products prior to smoking and sweet, smoothing rich, coumarin-like, creamy, rum-like, caramellic aroma and taste characteristics may be readily imparted to smoking tobacco products on smoking in the main stream and in the side stream and may be readily varied and controlled to produce the desired uniform flavoring and aroma characteristics.

In carrying out this aspect of our invention, we add to smoking tobacco materials or a suitable substitute therefor (e.g., dried lettuce leaves) an aroma and flavor additive containing as an active ingredient at least one or more of the oxybenzene derivatives of our invention.

In addition to one or more of the oxybenzene derivatives of our invention, other flavoring and aroma additives may be added to the smoking tobacco material or substitute therefor either separately or in the admixture with one or more of the oxybenzene derivatives of our invention as follows:

I. Synthetic Materials
Beta-ethyl-cinnamaldehyde;
Eugenol;
Dipentene;
β-Damascone;
β-Damascenone;
Maltol;
Ethyl maltol;
Delta undecalactone;

Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-2,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a,6,6,9a-tetramethyl naphtho-(2,1-b-)-furan;
4-Hydroxy hexanoic acid, gamma lactone;
Polyisoprenoid hydrocarbons defined in Example V of U.S. Pat. No. 3,589,372, issued on June 29, 1971

II. Natural Oils
Celery seed oil;
Coffee extract;
Bergamot Oil;
Cocoa extract;
Nutmeg oil; and
Origanum oil;

An aroma and flavoring concentrate containing one or more of the oxybenzene derivatives of our invention and if desired, one or more of the above indicated additional flavoring additives may be added to the smoking tobacco material, to the filter or to the leaf or paper wrapper. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste but insofar as the augmentation or the enhancement or the imparting of the sweet, coumarinic, creamy, heliotropin-like, fruity, rum-like and sugary aroma notes are concerned and insofar as the sweet, smoothing rich, coumarin-like, creamy, rum-like and caramellic aroma notes on smoking are concerned, we have found that satisfactory results are obtained if the proportion by weight of at least one or more of the oxybenzene derivatives of our invention to smoking tobacco material is between 100 ppm and 1,500 ppm (0.01%–0.15%) of at least one or more of the oxybenzene derivatives of our invention to the smoking tobacco material. We have found further, that satisfactory results are obtained if the proportion by weight of at least one or more of the oxybenzene derivatives of our invention used to flavoring materials is between 1,000 and 10,000 ppm (0.1–1.0%).

Any convenient method for incorporating one or more of the oxybenzene derivatives of our invention may be employed. Thus, one or more of the oxybenzene derivatives of our invention taken alone, or along with other flavoring additives may be dissolved in a suitable solvent such as ethanol, n-pentane, diethyl ether and/or other volatile organic solvents and the resulting solution may either be sprayed on the cured, cased and blended tobacco material or the tobacco material may be dipped into such solution. Under certain circumstances, a solution of one or more of the oxybenzene derivatives of our invention taken alone or further, together with other flavoring additives as set forth above, may be applied by means of a suitable applicator such as a brush or roller on the paper or leaf wrapper for the smoking product or it may be applied to the filter by either spraying, dipping or coating.

Furthermore, it will be apparent that only a portion of the tobacco or substitute therefor need be treated and the thus treated tobacco may be blended with other tobaccos before the ultimate tobacco product is formed. In such cases the tobacco treated may have one or more of the oxybenzene derivatives of our invention in excess of the amounts or concentrations above indicated so that when blended with other tobaccos, the final product will have the percentage within the indicated range.

In accordance with one specific example of our invention, an aged, cured and shredded domestic burley tobacco is spread with a 20% ethyl alcohol solution of the compound having the structure:

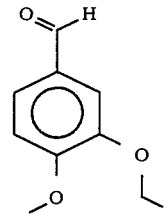

to provide a tobacco composition containing 800 ppm by weight of the compound having the structure:

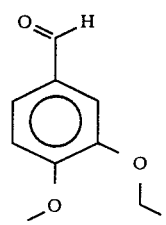

on a dry basis. Thereafter the alcohol is removed by evaporation and the tobacco is manufactured into cigarettes by the usual techniques. The cigarette, when treated as indicated, has a desired and pleasing aroma which is detectable in the main stream and the side stream when the cigarette is smoked. This aroma is described as being sweet, smoothing, rich, coumarin-like, creamy and caramellic.

While our invention is particularly useful in the manufacture of smoking tobacco, such as cigarette tobacco, cigar tobacco and pipe tobacco, other tobacco products formed from sheeted tobacco dust or fines may also be used. Likewise, one or more of the oxybenzene derivatives of our invention can be incorporated with material such as filter tip materials, seam paste, packaging materials and the like which are used along with tobacco to form a product adapted for smoking. Furthermore, one or more of the oxybenzene derivatives of our invention can be added to certain tobacco substitutes of a natural or synthetic origin (e.g., dried lettuce leaves) and, accordingly, by the term "tobacco" as used throughout this specification, is meant any composition intended for human consumption by smoking or otherwise, whether composed of tobacco plant parts or substitute materials or both.

One or more of the oxybenzene derivatives of our invention having the structures:

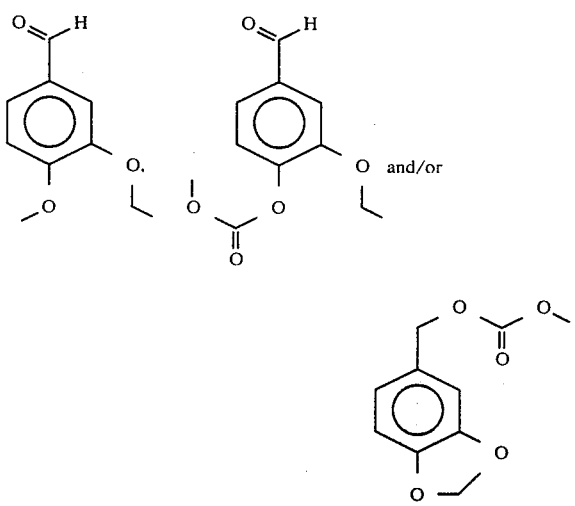
and/or and one or more auxilliary perfume ingredients including, for example, alcohols, aldehydes other than the aldehydes of our invention, nitriles, esters other than the esters of our invention, ketones, cyclic esters, ethers other than the ethers of our invention, synthetic essential oils and natural essential oils may be admixed so that the combined odor of the individual components produces a pleasant and desired fragrance particularly and preferably insofar as floral fragrances are concerned.

Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation and and (d) topnotes which are usually low-boiling, fresh smelling materials.

In perfume compositions, it is the individual components which contribute particular olfactory characteristics but the overall effect of the perfume composition will be the sum of the effects of each of the ingredients. Thus, one or a combination of oxybenzene derivatives of our invention can be used to alter the aroma characteristics of a perfume composition, for example, by utilizing or moderating the olfactory reaction contributed by another ingredient in the composition.

The amount of one or a combination of oxybenzene derivatives of our invention which will be effective in perfume compositions depends on many factors, including the other ingredients, their amounts and the effects which are desired. It has been found that perfume compositions containing as little as 0.05% of one or a combination of oxybenzene derivatives of our invention and even less (e.g., 0.02%) can be used to impart natural and diffusive vanilla-like, sweet, fruity, raspberry-like, anisic-like and ionone-like aroma nuances to soaps, cosmetics, solid or liquid anionic, cationic, nonionic or zwitterionic detergents, fabric softener compositions, fabric softener articles, perfumed polymers and other products. The amount employed can range up to 40% of the fragrance components and will depend on considerations of cost, nature of the end product, the effect desired on the finished product and the particular fragrance sought.

One or more of the oxybenzene derivatives of our invention are useful taken alone or in perfume compositions as an olfactory component in detergents and soaps, space odorants and deodorants, perfumes per se, colognes per se, toilet water, bath preparations such as bath oils and bath solids; hair preparations such as lacquers, brilliantines, pomades and shampoos; cosmetic preparations such as creams, deodorants, hand lotions and sun screens; powders such as talcs, dusting powders, face powders and the like. When used as an olfactory component, as little as 0.01% of the oxybenzene derivatives of our invention will suffice to impart a natural and diffusive vanilla-like, sweet, fruity, raspberry-like, anisic and ionone-like aroma profile to perfumed articles. Generally, no more than 3% of one or more of the oxybenzene derivatives of our invention based on the ultimate end product is required in the perfumed article.

Thus, insofar as perfumed articles are concerned, the amount of one or more of the oxybenzene derivatives of our invention can vary from 0.01% by weight up to 3.0% by weight based on the total weight of the perfumed article, that is, based on the total weight of such materials as anionic, cationic, nonionic, or zwitterionic solod or liquid detergent bases; or fabric softener compositions, or fabric softener articles, or perfumed polymers.

In addition, the perfume composition or fragrance composition of our invention can contain a vehicle or carrier for one or more of the oxybenzene derivatives of our invention. The vehicle can be a liquid such as a non-toxic alcohol, a non-toxic glycol or the like. The carrier can be an absorbent solid such as a gum (e.g., gum arabic, gum tragacanth, guar gum or xanthan gum) or components for encapsulating the composition (such as gelatin as by coacervation or a urea-formaldehyde prepolymer as by polymerization of a shell around a liquid center).

One or more of the oxybenzene derivatives of our invention can also be combined in proportions of from 0.1% up to 99.9% with respect to the benzodioxanones of U.S. Pat. No. 4,294,266 issued on Oct. 13, 1981, the specification of which is incorporated herein by reference. Thus, the instant invention not only contemplates the organoleptic utilities of one or more of the oxybenzene derivatives of our invention but also involves mixtures of one or more of the oxybenzene derivatives of our invention with the bicyclic compounds having the generic structure:

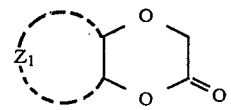

wherein $Z_1$ is benzo or cyclohexano.

It will thus be apparent that one or more of the oxybenzene derivatives of our invention taken alone or further together with the cyclic chemical compounds defined according to the structure:

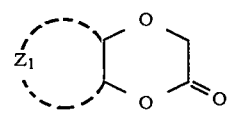

wherein $Z_1$ is benzo or cyclohexano can be utilized to alter the sensory properties of consumable materials particularly organoleptic properties such as flavors and/or fragrgances of a wide variety of consumable materials.

The following examples are illustrative and the invention is to be considered to be restricted thereto only as indicated in the appended claims.

All parts and percentages given are by weight unless otherwise specified.

EXAMPLE I

PREPARATION OF HELIOTROPYL METHYL CARBONATE

Reaction:

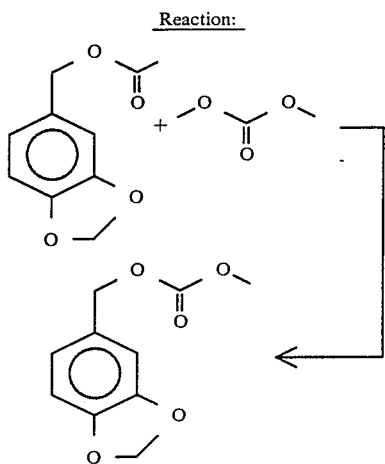

Into a 2 liter reaction vessel equipped with stirrer, thermometer, reflux condenser, addition funnel and Bidwell trap are placed 15 grams (0.28 moles) of powdered sodium methoxide and 500 grams (5.0 moles) of dimethyl carbonate. The resulting mixture is heated to 85° C. with stirring and over a period of 30 minutes 500 grams (2.6 moles) of heliotropyl acetate is added while distilling out the resulting methyl acetate via the Bidwell trap. During the addition of the heliotropyl acetate the reaction mass temperature is maintained at 85° C. At the end of the addition of the heliotropyl acetate, the reaction mass is continued to be stirred at 85°–90° C. for a period of 0.5 hours.

At the end of the 0.5 hour period, the reaction mass is cooled to 40° C. and 500 ml water and 250 ml methylene dichloride is added. The reaction mass now exists in two phases; an organic phase and an aqueous phase. The organic phase is separated from the aqueous phase and washed with one 500 ml portion of water. The resulting product is then stripped of solvent on a rotary evaporator and then distilled on a six inch stone packed column yielding the following fractions:

| Fraction No. | Vapor Temp. (°C.) | Liquid Temp. (°C.) | Vacuum mm. Hg. Pressure |
|---|---|---|---|
| 1 | 100/118 | 140/141 | 2.0/2.0 |
| 2 | 120 | 147 | 1.6 |
| 3 | 122 | 152 | 1.6 |
| 4 | 123 | 154 | 1.6 |
| 5 | 123 | 153 | 1.6 |
| 6 | 123 | 156 | 1.6 |
| 7 | 124 | 157 | 1.6 |
| 8 | 125 | 160 | 1.6 |
| 9 | 126 | 180 | 1.6 |
| 10 | 126 | 200 | 1.6 |

Figure 1:
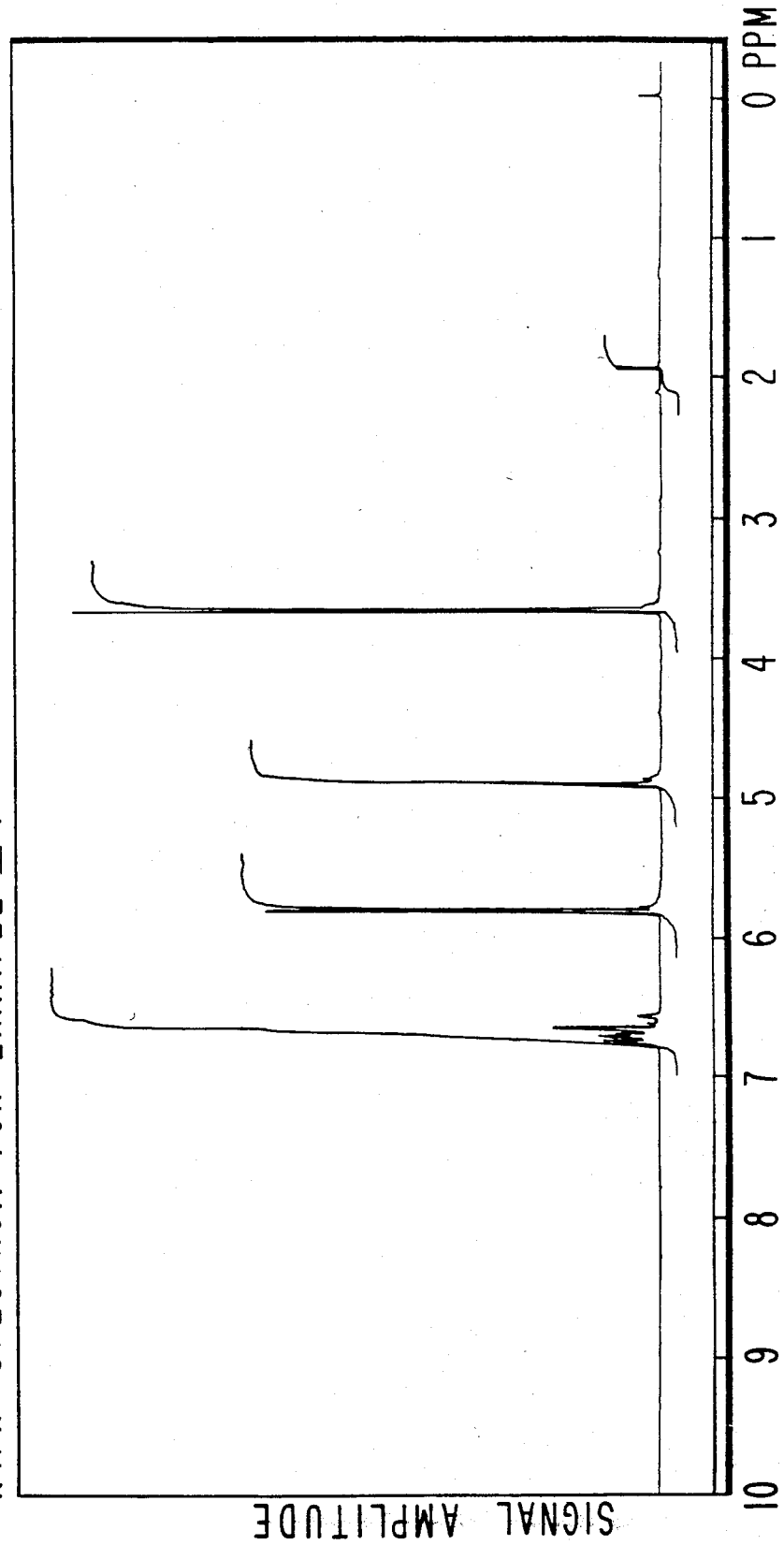
FIG. 1 is the NMR spectrum for the reaction product of Example I consisting of the compound having the structure.

FIG. 1 is the NMR spectrum for fraction 8 of the reaction product which is the compound having the structure:

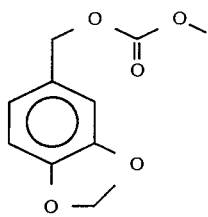

(CFCl$_3$ solvents; 100 MHz field strength).

FIG. 2 is the infra-red spectrum for fraction 8, which is the compound having the structure:

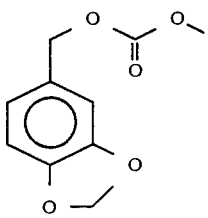

EXAMPLE II

A. PREPARATION OF ETHYL VANILLIN CARBONATE; AND

B. PREPARATION OF p-METHOXY-m-ETHOXY BENZALDEHYDE

Reactions:

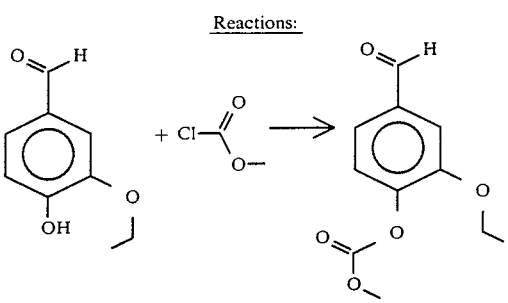

and

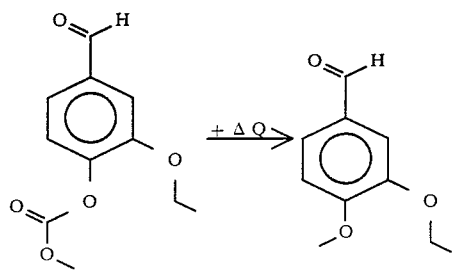

Into a 3 liter reaction flask equipped with nitrogen blanket apparatus, thermometer, reflux condenser and heating mantle is placed 315 grams (3 moles) of sodium carbonate, 1.6 liters of methylethyl ketone, 9 grams of Aliquat ®336 (capryltrimethyl ammonium chloride) and 500 grams (3 moles) of 3-ethoxy-4-hydroxybenzyldehyde. The resulting mixture is heated to reflux (69°

C.) and, while refluxing, 398 grams (4.2 moles) of methyl chloroformate is added over a 1 hour period to the reaction mass.

The reaction mass is continued to be refluxed at 65°–75° C. for a period of 14 hours. At the end of the 14 hour period, 100 grams additional methyl chloroformate is added to the reaction mass. The reaction mass is then refluxed again for a period of 5 hours, whereupon 220 grams of sodium carbonate and 200 grams of methyl chloroformate is added. The reaction mass is refluxed for an additional hour.

1 Liter of water is added to the reaction mass to dissolve the salts and excess methyl chloroformate. 6 Liters of water is then added to the reaction mass and the resulting aqueous phase is separated from the organic phase. The organic phase is washed with saturated sodium chloride followed by water. The aqueous phase is extracted with toluene and the organic phase is combined with the aqueous phase.

The resulting crude reaction product is then distilled on a 6 inch Rushover column yielding the following frations:

| Fraction No. | Vapor Temp. (°C.) | Liquid Temp. (°C.) | Vacuum mm. Hg. Pressure |
|---|---|---|---|
| 1 | 30/42 | 37/55 | 16/14 |
| 2 | 44 | 74 | 14.0 |
| 3 | 35 | 130 | 12.0 |
| 4 | 162 | 178 | 6.0 |
| 5 | 158 | 166 | 6.0 |
| 6 | 154 | 170 | 5.0 |
| 7 | 141 | 165 | 4.6 |
| 8 | 152 | 174 | 5.0 |
| 9 | 155 | 180 | 6.0 |
| 10 | 128 | 243 | 6.0 |

A portion of the reaction product having the structure:

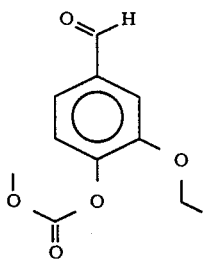

is isolated after the 1 hour reflux period with methyl chloro formate.

The remainder of the reaction product has the structure:

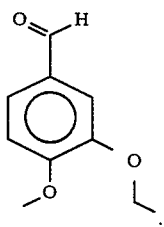

FIG. 3 is the GLC profile of the crude reaction product after 1 hour of refluxing. The peak on the GLC profile indicated by reference 31 is the peak for the starting material having the structure:

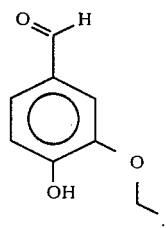

The peak on FIG. 3 indicated by reference 32 is for the reaction product having the structure:

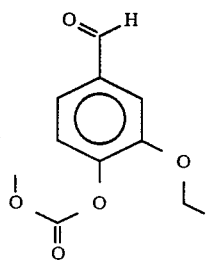

The conditions for the GLC profile are: 12% SF-96, 6'×¼" column, programmed from 100° to 220° C. at 8° C. per minute.

FIG. 4 is the NMR spectrum for the peak indicated by reference 32 of FIG. 3 for the compound having the structure:

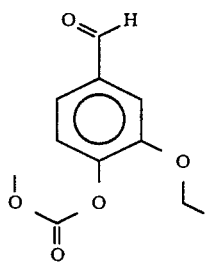

(solvent: CFCl₃; field strength 100 MHz).

FIG. 5 is the infra-red spectrum for the peak indicated by reference 32 of FIG. 3 for the compound having the structure:

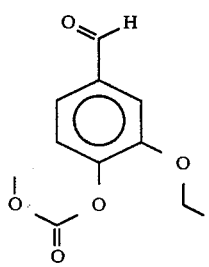

FIG. 6 is the GLC profile for Fraction 7 of the foregoing distillation containing the compound having the structure:

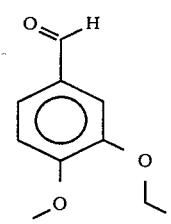

(conditions: 12% SF-96, 6'×¼" column, programmed from 100°–220° C. at 8° C. per minute).

FIG. 7 is the NMR spectrum for Fraction 7 of the foregoing distillation containing the compound having the structure:

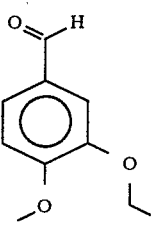

(solvent: CFCl$_3$; field strength 100 MHz).

FIG. 8 is the infra-red spectrum for Fraction 7 of the foregoing distillation containing the compound having the structure:

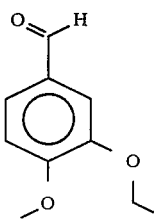

EXAMPLE III

PERFUME COMPOSITION

The following mixtures are prepared:

| Ingredients | Parts by Weight | |
|---|---|---|
| | III(A) | III(B) |
| Benzyl acetate | 50 | 50 |
| Rosewood oil | 100 | 100 |
| Cedarwood oil | 150 | 150 |
| Linalyl acetate | 100 | 100 |
| Alpha-ionone | 80 | 80 |
| Ethyl cinnamate | 20 | 20 |
| Amyl cinnamic aldehyde | 50 | 50 |
| Isoeugenol | 50 | 50 |
| Methyl-3-isopropyl-6-methyl-resorcylate | 50 | 50 |
| Musk xylene | 50 | 50 |
| Styrax resin | 100 | 100 |
| p-Methoxy, m-ethoxy benzaldehyde | 30 | 0 |
| Heliotropyl methyl carbonate | 0 | 30 |

The foregoing perfume formulation is an important part of the chypre essence. The coumarin ordinarily in this formulation has been replaced by either the p-methoxy, m-ethoxy benzaldehyde or the heliotropyl methyl carbonate.

Insofar as the replacement of the coumarin with the p-methoxy, m-ethoxy benzaldehyde produced according to Example II is concerned, this chypre essence has added to it the coumarin-like intensely vanillin-like aroma profile. Accordingly, the composition of Example III(A) can be described as "chypre with vanillin-like, coumarin-like undertones of very high intensity".

The replacement of the coumarin with the composition of matter of Example I containing the heliotropyl methyl carbonate gives rise to a chypre essence having added thereto coumarin-like, raspberry-like and ionone-like nuances with sweet, anisic topnotes.

Accordingly, the chypre essence of Example III(B) can be described as "chypre essence having coumarin-like, raspberry-like and ionone-like undertones and sweet, anisic topnotes".

EXAMPLE IV

FGOUGÈRE PERFUME FORMULATION

The following Fougère perfume formulations are prepared:

| Ingredients | Parts by Weight | |
|---|---|---|
| | IV(A) | IV(B) |
| Oakmoss absolute (50% in diethyl phthalate) | 2 | 2 |
| Bergamot oil | 15 | 15 |
| Lavender oil | 19 | 19 |
| Citronellol | 15 | 15 |
| Patchouli oil | 4 | 4 |
| Geranium oil | 5 | 5 |
| Gamma methyl ionone | 15 | 15 |
| Petitgrain oil | 2 | 2 |
| Musk ketone | 8 | 8 |
| Heliotropine | 2 | 2 |
| Clary sage oil | 2 | 2 |
| Amyl salicylate | 1 | 1 |
| 1,4-Benzodioxan-2-one | 10 | 10 |
| p-Methoxy, m-ethoxy benzaldehyde produced according to Example II | 5 | 0 |
| Ethyl vanillin carbonate produced according to Example II | 0 | 5 |

The 1,4-benzodioxan-2-one taken in combination with the p-methoxy, m-ethoxy benzaldehyde of our invention gives rise to surprising strength to this Fougère formulation and, in addition, acts as a fixative therefor. Addition of the mixture also creates a natural and diffusive coumarin-like, vanillin-like aroma in the case of Example IV(A). Accordingly, the fragrance of Example IV(A) can be termed as "Fougère with a natural and diffusive coumarin-like, vanillin-like undertone which is extremely powerful; 15–20 times that, when using vanillin itself".

The composition containing the vanillin ethyl carbonate prepared according to Example II adds to this Fougère formulation, a sweet, coumarin-like aroma with strong vanillin topnotes; 15 to 20 times stronger than using vanillin itself. Accordingly, the fragrance formulation of Example IV(B) can be described as "Fougère with an intense coumarin and vanillin undertone; ten times longer lasting than without the use of the vanillin ethyl carbonate".

EXAMPLE V

PERFUMED LIQUID DETERGENT

Concentrated liquid detergents with aroma nuances as set forth in Table II, infra, are prepared containing 0.10%, 0.15%, and 0.20% of one of the substances as set forth in Table II, infra. They are prepared by adding and homogeneously mixing the appropriate quantity of substance set forth in Table II, infra, in the liquid detergent. The detergents all possess aromas as set forth in Table II, infra:

TABLE II

| Perfume Substance | Aroma Profile |
| --- | --- |
| The compound having the structure: 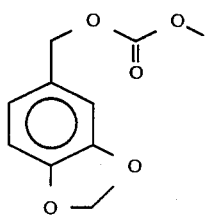 | A sweet, fruity, raspberry-like anisic-like, ionone-like aroma profile. |
| The compound having the structure: 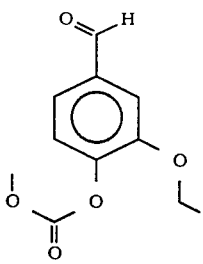 | A characteristic intense vanilla-like aroma having a strength of about 4 times that of vanillin and having coumarin-like undertones. |
| The compound having the structure: 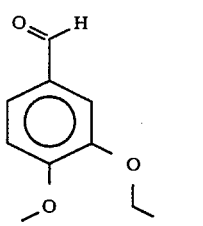 | A characteristic intense vanilla-like aroma having a strength of about 16 times that of vanillin and having the property that it does not give rise to any discoloration particularly in perfumed articles such as soap. The compound has coumarin-like undertones. |
| Perfume composition of Example III(A) | Chypre with vanillin-like, coumarin-like undertones of very high intensity. |
| Perfume composition of Example III(B) | Chypre essence having coumarin-like, raspberry-like and ionone-like undertones and sweet, anisic topnotes. |
| Perfume composition of Example IV(A) | Fougere with a natural and diffusive coumarin-like, vanillin-like undertone which is extremely powerful; 15–20 times that, when using vanillin itself. |
| Perfume composition of Example IV(B) | Fougere with an intense coumarine and vanillin undertone; 10 times longer lasting than without the use of the vanillin ethyl carbonate. |

EXAMPLE VI

PREPARATION OF COLOGNES AND HANDKERCHIEF PERFUMES

Each of the perfumery substances as set forth in Table II of Example V is incorporated individually into colognes at concentrations of 1.5%, 2.0%, 2.5%, 3.0%, 3.5% and 4.0% in 80%, 85%, and 90% aqueous ethanol; and into handkerchief perfumes at concentrations of 10%, 15%, 20% and 25% (in 80%, 85%, 90% and 95% aqueous ethanol compositions). In each of the compositions tested, distinct and definitive aromas as set forth in Table II of Example V are imparted to the colognes and to the handkerchief perfumes.

EXAMPLE VII

PREPARATION OF A SOAP COMPOSITION

One hundred grams of soap chips (IVORY ® manufactured by the Procter & Gamble Company of Cincinnati, Ohio) are mixed with one gram of each of the perfumery substances, on an individual basis, of Table II of Example V. The resulting mixture is melted and maintained at 8 atmospheres pressure and 150° C. for a period of 5 hours. The soap is then placed in molds and the thus formed liquid soap is cooled to room temperature. Each of the soap cakes is then aged for a period of one week under 8 atmospheres nitrogen pressure.

Each of the soap cakes manifests a pleasant aroma as set forth in Table II of Example V, supra.

EXAMPLE VIII

PREPARATION OF A SOLID DETERGENT COMPOSITION

A detergent is prepared from the following ingredients according to Example I of Canadian Patent No. 1,007,948, the specification of which is incorporated by reference herein.

| Ingredients | Parts by Weight |
| --- | --- |
| Neodol 45-11 (a $C_{14}$–$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

Each of the detergents is a "phosphate-free" detergent. A total of 100 grams of this detergent is admixed with 0.15 grams of each of the perfumery substances of Table II of Example V (on an individual basis). Each of the detergent samples has excellent diffusive aromas as set forth in Table II of Example V.

EXAMPLE IX

PERFUMED LIQUID DETERGENTS

Concentrated liquid detergents (lysine salt of n-dodecylbenzene sulfonic acid as more specifically described in U.S. Pat. No. 3,948,818, issued on Apr. 6, 1976, the specification of which is incorporated by reference herein) with aromas as set forth in Table II of Example V are prepared containing 0.50% of each of the perfumery formulations of Table II of Example V. They are prepared by adding and homogeneously mixing the appropriate quantity of perfume formulation in the liquid detergent. The detergents all possess aromas as set forth in Table II of Example V.

EXAMPLE X

FABRIC SOFTENER ARTICLE

Utilizing the procedure of Example I of column 15 of U.S. Pat. No. 3,632,396 (the disclosure of which is incorporated by reference herein) a non-woven cloth substrate useful as a drier-added fabric softening article of manufacture is prepared wherein the substrate, the substrate coating and the outer coating and the perfuming material are as follows:

1. a water dissolvable paper ("Dissolvo Paper") as the base
2. Adogen 448 (m.p. about 140° F.) as the substrate coating, and
3. an outer coating having the following formulation (m.p. about 150° F.):

| 57% | $C_{20-22}$ HAPS |
| 22% | isopropyl alcohol |
| 20% | antistatic agent |
| 1% | of each of the perfumery substances on an individual basis as set forth in Table II of Example V, supra. |

A fabric softening composition prepared as set forth above having aroma characteristics as set forth in Table II of Example V consists of a substrate having a weight of about 5 grams per 100 square inches; a substrate coating having a weight of about 1.85 grams per 100 square inches of substrate and an outer coating having a weight of about 1.4 grams per 100 square inches of substrate, thereby providing a total aromatized substrate and outer coating weight ratio of about 1:1 by weight of the substrate. The aromas as set forth in Table II of Example V are imparted in a pleasant manner to the head space in the drier on operation thereof using the said drier-added fabric softening non-woven fabric.

EXAMPLE XI

PERFUMED POLYMER

Scented polyethylene pellets having aromas as set forth in Table II of Example V are prepared according to the procedure of Example III of U.S. Pat. No. 3,505,432 issued on Apr. 7, 1970, the disclosure for which is incorporated by reference herein. Thus, 75 pounds of polyethylene having a melting point of about 220° F. are heated to about 230° F. in a container as illustrated in FIGS. 1 and 2 of U.S. Pat. No. 3,505,432. Twenty-five pounds of one of the perfume materials of Table II of Example V are then quickly added to the liquid polyethylene and the lid in the apparatus is put in place and the agitating means are actuated. The temperature is maintained at about 225° F. and the mixing is continued for about 5–15 minutes. The valve is then opened in order to allow flow of the molten polyethylene enriched with the scented material to exit through orifices in the apparatus. The liquid falling through the orifices solidifies almost instantaneously upon impact with the moving cooled conveyor part of the apparatus. The solid polyethylene beads or pellets having a pronounced scent as set forth in Table II of Example V are thus formed. Analysis demonstrates that the pellets contain almost about 25% of the particular perfume substance set forth in Table II of Example V so that almost no losses of the scenting substance occur. These pellets are called master pellets. Fifty pounds of the said master pellets are then added to 1,000 pounds of unscented polyethylene powder and the mass is heated to the liquid state. The liquid is molded into thin sheets or films. The sheets or films have a pronounced aroma as set forth in Table II of Example V. When polypropylene replaces the polyethylene, a substantially identical result occurs.

EXAMPLE XII

VANILLA FLAVOR

The following formulation is prepared:

| p-Methoxy, m-ethoxy benzaldehyde | 13.00 grams |
| Benzodihydropyrone | 3.00 grams |
| Heliotropin | 1.00 gram |
| Propenyl guiacol | 0.50 gram |
| Gamma nonyl lactone | 0.25 gram |
| Gamma undecalactone | 0.25 gram |
| Delta dodecalactone | 0.25 gram |
| 4,4A,5,6-tetrahydro-7-methyl-2-(3H)—naphthalenone having the structure: | 0.10 grams |

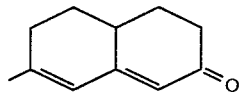

produced according to
Example III of Application
for U.S. Letters Pat.
Ser. No. 354,111 filed
on March 2, 1982

The p-methoxy, m-ethoxy benzaldehyde produced according to Example II imparts an intense vanilla nuance 15–20 times as intense as when using vanillin and 4–5 times as intense as when using ethyl vanillin.

Furthermore, the 4,4A,5,6-tetrahydro-7-methyl-2-(3H)-naphthalenone having the structure:

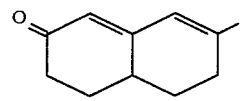

enhances the foregoing vanilla formulation (a) making it more natural-like, (b) imparting a coumarin-like, coconut-like aroma and a coumarin-like, coconut-like, almond-like, macaroon-like taste. The formulation is three times as powerful as the formulation without this compound added thereto. In addition, the formulation is rendered much more outstanding in a standard Creme-de-Kahlua formulation causing the Creme-de-Kahlua formulation to be more natural-like and preferred by a bench panel of five members, unanimously. The resulting formulation containing (i) the compound having the structure:

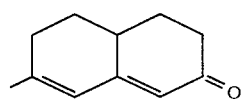

and (ii) the compound having the structure:

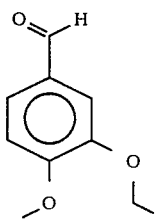

is added to the following liqueur formulation:

| Ingredients | Parts by Weight |
|---|---|
| Clove essential oil | 780 |
| Lemon essential oil | 400 |
| Orange essential oil | 300 |
| Cinnamon essential oil | 250 |
| Mace essential oil | 180 |
| Vanillin formulation (as set forth above) | 150 |
| Neroli essential oil | 10 |
| Citronellol | 2 |
| Rose absolute | 1 |
| Food grade ethanol | 927 |

The resulting liqueur is added to the following mixture in order to produce a consumable commercial material:

| Ingredients | Parts by Weight |
|---|---|
| 96% food grade ethanol | 301 kg |
| Sugar | 40 kg |
| Distilled water | 46.8 liters |
| Flavor (as set forth above) (0.5% in food grade ethanol) | 0.5 kg |

The resulting liqueur has an interesting, vanilla/bitter almond taste and aroma with coconut nuances making it useful as such or as a "Bagne" for a sauce used for soaking pound cakes such as "Rum BaBa".

EXAMPLE XIII

The vanilla flavor of Example XII is placed into an ice cream mix at the rate of 0.10%. The resulting previously-unflavored ice cream has a powerful vanilla flavor, unexpectedly 15-20 times as powerful as vanilla flavor using standard vanillin and 4-5 times as powerful as vanilla flavor using ethyl vanillin alone.

EXAMPLE XIV

BASIC WALNUT FLAVOR FORMULATION

The following basic walnut formulation is prepared:

| Ingredients | Parts by Weight |
|---|---|
| Cyclotene | 4.0 |
| Vanillin methyl carbonate | 0.1 |
| Butylisovalerate | 2.0 |
| Benzaldehyde | 6.0 |
| 2,3-diethyl pyrazine (10% in food grade ethanol) | 2.0 |
| Ethyl-2-methyl valerate | 2.0 |
| Gamma butyrolactone | 20.0 |
| Gamma hexenolactone | 10.0 |
| 2,4-decadienal (0.1% in food grade ethyl alcohol) | 0.5 |
| 2,4-heptadienal (0.1% in food grade ethyl alcohol) | 0.5 |
| Butylidene phthalide | 2.0 |

| Ingredients | Parts by Weight |
|---|---|
| Propylene glycol USP | 95.0 |

The formulation is divided into two parts. To one of the parts 0.8% by weight of the 86% composition of 4,4A,5,6-tetrahydro-7-methyl-2-(3H)-naphthalenone having the structure:

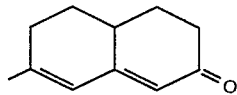

produced according to Example IV of Application for U.S. Letters Patent, Ser. No. 354,111 filed on Mar. 2, 1982 distillation fraction 8, is added. To the second part of the walnut formulation, nothing else is added. Both formulations with and without the additional material are compared at the rate of 100 ppm in water by a bench panel. Although all members of the bench panel prefer the walnut flavor with the addition of the compound having the structure:

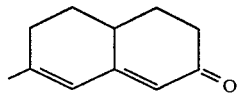

as a result of the additional characteristic walnut notes and bittermouth feel effects being present, both formulations are preferred over formulations wherein the p-methoxy, m-ethoxy benzaldehyde is substituted by 1.0 parts by weight of vanillin in view of the fact that the use of the vanillin methyl carbonate is much more "natural-like" insofar as its vanilla nuances are concerned.

EXAMPLE XV

A. Powder Flavor Composition

Twenty grams of the flavor composition of Example XIV is emulsified in a solution containing 300 grams gum acacia and 700 grams of water. The emulsion is spray dried with a Bowen Lab Model Drier utilizing 260 c.f.m. of air with an inlet temperature of 500° F. and an outlet temperature of 200° F. and a wheel speed of 50,000 rpm.

B. Sustained Release Flavor

The following mixture is prepared:

| Ingredient | Parts by Weight |
|---|---|
| Liquid walnut flavor composition of Example XIV | 20 |
| Propylene glycol | 9 |
| Cab-O-Sil ® M-5 (brand of silica produced by the Cabot Corp. of 125 High St., Boston, Mass. 02110 | |
| Physical properties: Surface area: 200 m²/gm Nominal particle size: 0.012 microns Density: 2.3 lbs/cu. ft.) | 5 |

The Cab-O-Sil ® is dispersed in the liquid walnut flavor composition of Example XIV with vigorous stirring thereby resulting in a viscous liquid. Seventy-one parts by weight of the powder flavor composition of Part A, supra, is then blended into said viscous liquid with stirring at 25° C. for a period of 30 minutes resulting in a dry, free-flowing sustained release flavor powder.

EXAMPLE XVI

Ten parts by weight of 50 Bloom pigskin gelatin is added to ninety parts by weight of water at a temperature of 150° F. The mixture is agitated until the gelatin is completely dissolved and the solution is cooled to 120° F. Twenty parts by weight of the liquid flavor composition of Example XIV is added to the solution which is then homogenized to form an emulsion having a particle size typically in the range of 2-5 microns. The material is kept at 120° F. under which conditions the gelatin will not gel.

Coacervation is induced by adding slowly and uniformly, forty parts by weight of a 20% aqueous solution of sodium sulphate. During coacervation of gelatin, molecules are deposited uniformly about each oil droplet as a nucleus.

Gelation is effected by pouring the heated coacervate mixture into 1,000 parts by weight of a 7% aqueous solution of sodium sulphate at 65° F. The resulting gelled coacervate may be filtered and washed with water at temperatures below the melting point of gelation, to remove the salt.

Hardening of the filter cake, in this example, is effected by washing with 200 parts by weight of 37% solution of formaldehyde in water. The cake is then washed to remove the residual formaldehyde.

EXAMPLE XVII

CHEWING GUM

One hundred parts by weight of chicle are mixed with four parts by weight of the flavor prepared in accordance with Example XV, Part B. Three hundred parts of sucrose and one hundred parts of corn syrup are added. Mixing is effected in a ribbon blender with jacketed side walls of the type manufactured by the Baker Perkins Co.

The resultant chewing gum blend is then manufactured into strips one inch in width and 0.1 inches in thickness. The strips are cut into lengths of three inches each. On chewing, the chewing gum has a pleasant, long-lasting sweet, fruity, walnut flavor.

EXAMPLE XVIII

CHEWING GUM

One hundred parts by weight of chicle are mixed with eighteen parts by weight of the flavor prepared in accordance with Example XV. Three hundred parts of sucrose and one hundred parts of corn syrup are then added. Mixing is effected in a ribbon blender with jacketed side walls of the type manufactured by the Baker Perkins Co.

The resultant chewing gum blend is then manufactured into strips one inch in width and 0.1 inches in thickness. The strips are cut into lengths of three inches each. On chewing, the chewing gum has a pleasant, long-lasting sweet, fruity, walnut flavor.

EXAMPLE XIX

TOOTHPASTE FORMULATION

The following separate groups of ingredients are prepared:

| Parts by Weight | Ingredients |
|---|---|
| Group "A" | |
| 30.200 | Glycerine |
| 15.325 | Distilled water |
| 0.100 | Sodium benzoate |
| 0.125 | Saccharin sodium |
| 0.400 | Stannous fluoride |
| Group "B" | |
| 12.500 | Calcium carbonate |
| 37.200 | Dicalcium phosphate (dihydrate) |
| Group "C" | |
| 2.000 | Sodium n-lauroyl sarcosinate (foaming agent) |
| Group "D" | |
| 1.200 | Flavor material of Example XV, Part B |
| 100.000 (total) | |

Procedures:
1. The ingredients in Group "A" are stirred and heated in a steam jacketed kettle to 160° F.
2. Stirring is continued for an additional three to five minutes to form a homogeneous gel.
3. The powders of Group "B" are added to the gel, while mixing until a homogeneous paste is formed.
4. With stirring, the flavor of "D" is added and lastly, the sodium n-lauroyl sarcosinate.
5. The resultant slurry is then blended for one hour.

The completed paste is then transferred to a three roller mill and then homogenized, and finally tubed.

The resulting toothpaste, when used in a normal toothbrushing procedure, yields a pleasant, sweet, walnut flavor of constant strong intensity throughout said procedure (1-1.5 minutes).

EXAMPLE XX

CHEWABLE VITAMIN TABLETS

The flavor material produced according to the process of Example XV, Part B, is added to a chewable vitamin tablet formulation at a rate of 10 gm/kg which chewable vitamin tablet formulation is prepared as follows:

In a Hobart Mixer, the following materials are blended to homogeneity:

| Ingredients | Gms/1000 Tablets |
|---|---|
| Vitamin C (ascorbic acid as ascorbic acid-sodium ascorbate mixture 1:1) | 70.000 |
| Vitamin $B_1$ (thiamine mononitrate) as Rocoat ® thiamine mononitrate 33⅓% (Hoffman LaRoche) | 4.000 |
| Vitamin $B_2$ (riboflavin) as Rocoat ® riboflavin 33⅓% | 5.000 |
| Vitamin $B_6$ (pyridoxine hydrochloride) as Rocoat ® pyridoxine hydrochloride 33⅓% | 4.000 |
| Niacinamide as Rocoat ® niacinamide 33⅓% | 33.000 |
| Calcium pantothenate | 11.500 |
| Vitamin $B_{12}$ (cyanocobalamin) as Merck 0.1% in gelatin | 3.500 |
| Vitamin E (dl-alpha tocopheryl acetate) as dry Vitamin E acetate 33⅓% Roche | 6.600 |
| d-Biotin | 0.044 |
| Certified lake color | 5.000 |
| Flavor of Example XV, Part B | as indicated above |

| Ingredients | Gms/1000 Tablets |
| --- | --- |
| Sweetener sodium saccharin | 1.000 |
| Magnesium stearate lubricant | 10.000 |
| Mannitol q.s. to make | 500.000 |

Preliminary tablets are prepared by slugging with flatfaced punches and grinding the slugs to 14 mesh. 13.5 grams dry Vitamin A acetate and 0.6 grams Vitamin D are then added as beadlets. The entire blend is then compressed using concave punches at 0.5 grams each.

Chewing of the resultant tablets yields a pleasant, long-lasting, consistently strong, sweet, walnut flavor for a period of 12 minutes.

EXAMPLE XXI

CHEWING TOBACCO

Onto 100 pounds of tobacco for chewing (85% Wisconsin leaf and 15% Pennsylvania leaf) the following casing is sprayed at a rate of 30%:

| Ingredients | Parts by Weight |
| --- | --- |
| Corn syrup | 60.0 |
| Licorice | 10.0 |
| Glycerine | 20.0 |
| Fig juice | 4.6 |
| Prune juice | 5.0 |
| Flavor material of Example XV, Part B | 0.4 |

The resultant product is redired to a moisture content of 20%. On chewing, this tobacco has an excellent substantially consistent, long-lasting, sweet, green, walnut (20 minutes) nuance in conjunction with the main fruity tobacco note.

EXAMPLE XXII

SMOKING TOBACCO FORMULATION

A tobacco mixture is produced by admixing the following ingredients:

| Ingredients | Parts by Weight |
| --- | --- |
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

Cigarettes are prepared from this tobacco.
The following flavor formulation is prepared:

| Ingredients | Parts by Weight |
| --- | --- |
| Ethyl butyrate | 0.05 |
| Ethyl valerate | 0.05 |
| Maltol | 2.00 |
| Cocoa extract | 26.00 |
| Coffee extract | 10.00 |
| Ethyl alcohol | 20.00 |
| Water | 41.90 |

The above stated tobacco formulation is applied at the rate of 0.1% to all of the cigarettes produced using the above tobacco formulation. One-third of the cigarettes are then treated with 500 or 1,000 ppm of p-methoxy, m-ethoxy benzaldehyde produced according to Example II having the structure:

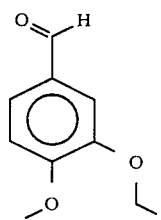

One-third of the cigarettes are also treated with 500 or 1,000 ppm of vanillin ethyl carbonate having the structure:

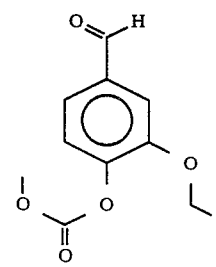

prepared according to Example II.

Control cigarettes not containing p-methoxy, m-ethoxy benzaldehyde or vanillin ethyl carbonate produced according to Example II and the experimental cigarettes which do contain the p-methoxy, m-ethoxy benzaldehyde or ethyl vanillin carbonate prepared according to Example II are then evaluated by paired comparison and the results are as follows:

The experimental cigarettes containing the p-methoxy, m-ethoxy benzaldehyde or ethyl vanillin carbonate have sweet, creamy, coumarin-like aroma nuances both prior to smoking; and sweet, smoothing rich, coumarin-like and vanillin-like aroma and taste nuances on smoking in the main stream and the side stream.

The experimental cigarettes containing the ethyl vanillin carbonate produced according to Example II have, prior to smoking, sweet, coconut-like, and vanillin-like aromas on smoking and sweet, creamy, coconut-like, vanillin-like and caramellic-like aromas in the main stream and the side stream.

In general, the products of Example II enhance the tobacco-like taste and aroma of blended cigarettes imparting to them in general, sweet and vanilla-like tobacco notes.

EXAMPLE XXIII

FLAVORED FOODSTUFF 2.25 Ounces of a coconut macaroon mix distributed by Drake Bakeries, Division of Borden, Inc. of Columbus, Ohio 43215 is intimately admixed at the level of 10 ppm with (i) p-methoxy, m-ethoxy benzaldehyde produced according to Example II or (ii) ethyl vanillin carbonate produced according to Example II.

The coconut macaroon composition contains corn syrup, coconut, sugar and egg whites.

The coconut macaroon composition is then baked at 325° F. at atmospheric pressure for a period of 20 minutes. The resultant coconut macaroon cookies have an excellent "natural coconut", intense vanilla note not present in the cookies without the composition of Example II.

When 2 ppm of 4,4A,5,6-tetrahydro-7-methyl-2-(3H)-naphthalenone produced according to Example III of Application for U.S. Letters Patent, Ser. No. 354,111 filed on Mar. 2, 1982 the specification for which is incorporated by reference herein, is also added, the coconut macaroon composition also contains intense, coumarin-like notes not present in the cookies without such compositions.

EXAMPLE XXIV

The following formulation is prepared:

| Ingredient | Parts by Weight |
|---|---|
| para-hydroxybenzyl acetone | 4 |
| vanillin | 1 |
| maltol | 2 |
| α-ionone (10% in propylene glycol) | 2 |
| isobutyl acetate | 20 |
| ethyl butyrate | 5 |
| dimethyl sulfide | 1 |
| acetic acid | 10 |
| acetaldehyde | 15 |
| propylene glycol | 940 |

Heliotropyl methyl carbonate [3,4-(methylene dioxy)] benzyl alcohol methyl carbonate having the structure:

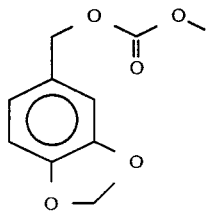

prepared according to the process of Example I is added to a portion of the above formulation at the rate of 0.4%. The heliotropyl methyl carbonate is compared with the formulation without said heliotropyl methyl carbonate at the rate of 0.01% (100 ppm) in water by a bench panel. The flavor containing the heliotropyl methyl carbonate is determined to have the aroma of fresh full ripened raspberries with the taste of ripe fruit and its seedy raspberry kernel, jammy, ionone-like nuances. In addition, there is a pleasant aesthetically pleasing anisic undertone in this formulation. These notes are not present in the formulation without the inclusion of the heliotropyl methyl carbonate having the structure:

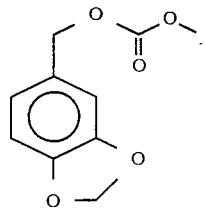

When the material containing the heliotropyl methyl carbonate is also admixed with 2-(4-hydroxy-4-methylpentyl) norbornadiene prepared according to Example II of U.S. Pat. No. 3,911,028 the specification for which is incorporated by reference herein at the rate of 0.005%, the raspberry formulation is still further strengthened.

EXAMPLE XXV

The following mixture is prepared:

| Ingredients | Parts by Weight |
|---|---|
| Natural Raspberry Concentrate Juice | 2½% |
| Water | 85% |
| Sugar syrup (37.5° Baume) | 12½% |

The ripened raspberry and seedy, raspberry kernel note of this raspberry juice is imparted increased strength by the addition of the heliotropyl methyl carbonate at the rate of from 0.02 parts per million to 10 parts per million.

EXAMPLE XXVI

To the raspberry formulation of Example XXIII, heliotropyl methyl carbonate produced according to Example I at the rate of 0.2% is added. This material is then called the "test composition". The raspberry formulation without the heliotropyl methyl carbonate is called the "control composition".

The test and control compositions are added to the food products described hereinafter in the proportions shown for 10 kilograms of material to be flavored:

Pudding—5-10 grams (0.15-1%)
Cooked sugar—15-20 grams (0.15-2%)
Cooked sugar—100 ml of sugar syrup (prepared by dissolving 1 kelogram of sucrose in 600 ml of water) and 20 grams of glucose are mixed together and slowly heated to 145° C. The flavor is added and the mass allowed to cool and harden.

Pudding—To 500 ml of warmed milk are added with stirring a mixture of 60 grams sucrose and 3 grams of pectin. The mixture is boiled for a few seconds and the flavor is added. The mixture was allowed to cool.

The finished foodstuff samples are tested by a panel of trained persons who express their views about the flavor of the samples. All member of the panel prefer the test samples having a more distinguished ripened raspberry aroma with the taste of the ripe raspberries and its seedy kernel note.

What is claimed is:

1. The process for preparing the compound having the structure:

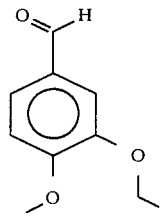

comprising the step of reacting the compound having the structure:

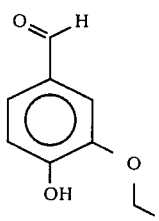
with methyl chloroformate at reflux conditions in the presence of a phase transfer agent and a base and in the presence of an inert solvent for such a period of time as to convert the entire reaction product to the compound having the structure:
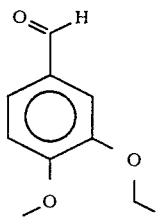
* * * * *